United States Patent
Amit et al.

(10) Patent No.: US 10,240,132 B2
(45) Date of Patent: Mar. 26, 2019

(54) COMPOSITION AND METHOD FOR TREATING ANDROGEN-DEPENDENT DISORDERS

(71) Applicant: TECHNION RESEARCH & DEVELOPMENT FOUNDATION LTD., Haifa (IL)

(72) Inventors: Roee Amit, Haifa (IL); Alexey Tomsov, Karmiel (IL); Orna Atar, Haifa (IL); Liron Abrahami, Kibbutz Ma'agan Michael (IL); Yael Annis, Hashmonaim (IL); Roni Cohen, Zikhron Ya'akov (IL); Alexandra Ereskovsky, Nesher (IL); Noa Katz, Haifa (IL); Lior Levy, Haifa (IL); Maayan Lufton, Kiryat Yam (IL); Tal Ofek, Haifa (IL); Sagi Sheinkman, Netanya (IL); Nitzan Shmuel, Nofit (IL); Inbal Vaknin, Or Akiva (IL); Ruth Veksler, Karmiel (IL); Adi Yannai, Haifa (IL)

(73) Assignee: TECHNION RESEARCH & DEVELOPMENT FOUNDATION LTD., Haifa (IL)

( * ) Notice: Subject to any disclaimer, the term of this patent is extended or adjusted under 35 U.S.C. 154(b) by 0 days.

(21) Appl. No.: 15/471,194

(22) Filed: Mar. 28, 2017

(65) Prior Publication Data

US 2017/0275596 A1 Sep. 28, 2017

Related U.S. Application Data

(60) Provisional application No. 62/396,167, filed on Sep. 18, 2016, provisional application No. 62/313,996, filed on Mar. 28, 2016.

(51) Int. Cl.
| | |
|---|---|
| C07H 21/04 | (2006.01) |
| C12N 9/04 | (2006.01) |
| A61K 35/742 | (2015.01) |
| A61K 38/44 | (2006.01) |
| A61K 9/00 | (2006.01) |
| C07K 1/00 | (2006.01) |
| C07K 19/00 | (2006.01) |
| A61K 38/00 | (2006.01) |

(52) U.S. Cl.
CPC .......... *C12N 9/0006* (2013.01); *A61K 9/0014* (2013.01); *A61K 35/742* (2013.01); *A61K 38/443* (2013.01); *C07K 1/00* (2013.01); *C07K 19/00* (2013.01); *C12Y 101/01225* (2013.01); *A61K 38/00* (2013.01); *Y02A 50/473* (2018.01)

(58) Field of Classification Search
CPC .................................................. C12N 9/0006
See application file for complete search history.

(56) References Cited

FOREIGN PATENT DOCUMENTS

WO WO-2010053199 A1 * 5/2010 ........... A61K 38/443

OTHER PUBLICATIONS

Oh et al., Temporal Stability of the Human Skin Microbiome, Cell Press, May 5, 2016, pp. 854-866, vol. 165 issue 4.
Grice et al., Topographical and Temporal Diversity of the Human Skin Microbiome, Science, May 29, 2009, pp. 1-7, vol. 324 issue 5931.
Dorrestein et al., Microbial Skin Inhabitants: Friends Forever; Cell Press, May 5, 2016, pp. 771-772, vol. 165 issue 4.
Chen et al., Skin Microbiota-Host Interactions, Nature, Jan. 25, 2018, pp. 427-436, vol. 553, Macmillan Publishers Limited.
Ellis et al., Male Pattern Baldness; Current Treatments, Future Prospects, Drug Discovery Today, Sep. 2008, pp. 791-797, vol. 13 issue 17/18.
Gonzalez et al., Androgenetic alopecia in the paediatric population: a retrospective review of 57 patients, British Journal of Dermatology, Mar. 9, 2010, pp. 378-385.
Adil et al., The effectiveness of treatments for adrongenetic alopecia: A systematic review and meta-analysis, Journal of American Academy of Dermatology, Inc., Apr. 7, 2017, pp. 136-141, vol. 77 issue 1.
Takayasu et al., The conversion of testosterone to 17-hydroxy-5-androstan-3-one (dihydrotestosterone) by human hair follicles. J Clin Endocrinol Metab. 1972, pp. 1098-1101, vol. 34 issue 6.
Olsen et al., The importance of dual 5a-reductase inhibition in the treatment of male pattern hair loss: Results of a randomized placebo-controlled study of dutasteride versus finasteride, Journal of American Academy of Dermatology, Inc., 2006, pp. 1014-1023, vol. 55 issue 6.
Kaufman et al., Finasteride in the treatment of men with adrogenetic alopecia, Journal of the American Academy of Dermatology, Oct. 1998, pp. 578-589, vol. 39 issue 4 part 1.
Liao et al., Effectiveness of a Layer-by-Layer Microbubbles-Based Delivery System for Applying Minoxidil to Enhance Hair Growth, Theranostics, Apr. 11, 2016, pp. 817-827, vol. 6 issue 6.
Lin et al., Expression and Characterization of Recombinant Type 2 3a-Hydroxysteroid Dehydrogenase (HSD) from Human Prostate: Demonstration of Bifunctional 3a/17b-HSD Activity and Cellular Distribution, Molecular Endocrinology, 1997, pp. 1971-1984, vol. 11 issue 13.
Askonas et al., The kinetic mechanism catalysed by homogeneous rat liver 3a-hydroxysteroid dehydrogenase: Evidence for binary and ternary dead-end complexes containing non-steroidal anti-inflammatory drugs, Biochemical Journal, 1991, pp. 835-841, vol. 278.

(Continued)

*Primary Examiner* — Albert M Navarro
(74) *Attorney, Agent, or Firm* — The Roy Gross Law Firm, LLC; Roy Gross

(57) ABSTRACT

Chimeric polypeptides comprising a dihydrotestosterone (DHT) reductase moiety, such as 3 alpha-hydroxysteroid dehydrogenase (3α-HSD), fused to a signal peptide moiety, polynucleotides encoding same, and compositions comprising at least one microorganism cell capable of secreting the chimeric polypeptide, are provided. Further provided are methods and kits for treating, preventing or ameliorating androgen-dependent disorders, including but not limited to androgenic alopecia.

14 Claims, 6 Drawing Sheets

Specification includes a Sequence Listing.

(56) References Cited

OTHER PUBLICATIONS

Wang et al., A new potential secretion pathway for recombinant proteins in Bacillus subtilis, Microbial Cell Factories, 2015, pp. 1-7, vol. 14 issue 179.

van Dijl et al., Bacillus subtilis: from soil bacterium to super-secreting cell factory, Microbial Cell Factories, 2013, pp. 1-6, vol. 12 issue 3.

Kang et al., Molecular engineering of secretory machinery components for high-level secretion of proteins in *Bacillus* species, Society for Industrial Microbiology and Biotechnology, Sep. 12, 2014, pp. 1599-1607, vol. 41, Springer.

Hoffman, "Intelligent" Polymers in Medicine and Biotechnology, Artificial Organs, 1995, pp. 458-467, vol. 19 issue 5, International Society for Artificial Organs, Blackwell Science, Inc.

Liu et al, Biomedical nanoparticle carriers with combined thermal and magnetic responses, Nano Today, Oct. 13, 2009, pp. 52-65, vol. 4, Elsevier.

Kong et al., Performing skin microbiome research: A method to the madness, J Invest Dermatol., Jun. 13, 2017, pp. 561-568, vol. 137 issue 3.

Meighan et al., Genetics of Bacterial Bioluminescence, Annu. Rev. Genet. 1994, pp. 117-139, vol. 28, Annual Reviews Inc.

La Rosa et al., Construction and Application of a luxABCDE Reporter System for Real-Time Monitoring of *Enterococcus faecalis* Gene Expression and Growth, Applied and Environmental Microbiology, Oct. 2012, pp. 1003-7011, vol. 78 issue 19.

Radeck et al., The Bacillus BioBrick Box: generation and evaluation of essential genetic building blocks for standardized work with Bacillus subtilis, Journal of Biological Engineering, 2013, pp. 1-16, vol. 7 issue 29, BioMed Central.

Chen et al., Combinatorial Sec pathway analysis for improved heterologous protein secretion in Bacillus subtilis: identification of bottlenecks by systematic gene overexpression, Microbial Cell Factories, 2015, pp. 1-15, vol. 14 issue 92, BioMed Central.

Hemmerich et al., Use of a Sec signal peptide library from Bacillus subtilis for the optimization of cutinase secretion in Corynebacterium glutamicum, Microbial Cell Factories, 2016, pp. 1-11, vol. 15 issue 208, BioMed Central.

Soerensen et al., Infrared skin temperature measurements for monitoring health in pigs: a review, Acta Veterinaria Scandinavica, 2015, pp. 1-11, vol. 57 issue 5.

Olm et al., Identical bacterial populations colonize premature infant gut, skin, and oral microbiomes and exhibit different in situ growth rates, Genome Research, 2017, pp. 610-612, vol. 27, Cold Spring Harbor Laboratory Press.

Caporaso, QIIME allows analysis of high-throughput community sequencing data, Nature Methods, May 2010, pp. 335-336, vol. 7 issue 5.

Martin, Cutadapt removes adapter sequences from high-throughput sequencing reads, EMBnet.journal, 2011, pp. 10-12, vol. 17.1.

Wilson, Microbial Inhabitants of Humans: Their ecology and role in health and disease, 2005, pp. 1-9, Cambridge University Press.

Olmez et al., Modeling the growth kinetics of Bacillus cereus as a function of temperature, pH, sodium lactate and sodium chloride concentrations, International Journal of Food Microbiology, 2005, pp. 135-143, vol. 98, Science Direct.

Saegusa et al., Usefulness of Infrared Thermometry in Determining Body Temperature in Mice, Laboratory Animal Science, Aug. 12, 2003, pp. 1365-1367, vol. 65 issue 12.

Stadlbauer et al., Lactobacillus casei Shirota Supplementation Does Not Restore Gut Microbiota Composition and Gut Barrier in Metabolic Syndrome: A Randomized Pilot Study, PLOS One, Oct. 28, 2015, pp. 1-14.

Engel et al., Standard methods for research on Apis mellifera gut symbionts, Journal of Apicultural Research, May 20, 2013, pp. 1-24, vol. 52 issue 4.

Belheouane et al., Improved detection of gene-microbe interactions in the mouse skin microbiota using high-resolution QTL mapping of 16S rRNA transcripts, Microbiome, 2017, pp. 1-17, vol. 5 issue 59.

Ke et al., A sensitive, simple and robust LC-MS/MS method for the simultaneous quantification of seven androgen- and estrogen-related steroids in postmenopausal serum, Journal of Steroid Biochemistry & Molecular Biology, 2014, pp. 523-534, vol. 144.

Schindelin et al., Fiji—an Open Source platform for biological image analysis, Nat Methods, 2012, pp. 1-15, vol. 9 issue 7.

Hall et al., Engineered Luciferase Reporter from a Deep Sea Shrimp Utilizing a Novel Imidazopyrazinone Substrate, ACS Chem. Biol. 2012, pp. 1848-1857, vol. 7 issue 11.

Castelino et al., Optimisation of methods for bacterial skin microbiome investigation: primer selection and comparison of the 454 versus MiSeq platform, BMC Microbiology, 2017, pp. 1-12, vol. 17 issue 23.

Metcalf et al., A microbial clock provides an accurate estimate of the postmortem interval in a mouse model system, eLife, 2013, pp. 1-19.

Bouslimani et al., Molecular cartography of the human skin surface in 3D, Proc Natl Acad Sci USA, Mar. 30, 2015, pp. 2120-2129.

Oh et al., Biogeography and individuality shape function in the human skin metagenome, Nature, Oct. 2, 2014, pp. 59-77, vol. 514, Macmillan Publishers Limited.

HiMedia Laboratories. Luria Broth Technical Data M575. 2015.

Tretera et al., Washing-resistant surfactant coated surface is able to inhibitpathogenic bacteria adhesion, Applied Surface Science, Mar. 1, 2014, pp. 147-154, issue 303, Elsevier.

Kimoto et al., Rattus norvegicus aldo-keto reductase family 1, member C14 (Akr1c14), mRNA. NCBI. https://www.ncbi.nlm.nih.gov/nuccore/NM_138547.3. Published 2010.

3-alpha-hydroxysteroid dehydrogenase. uniprot. http://www.uniprot.org/uniprot/P23457. Accessed Jan. 1, 2017.

Owen et al., A direct assay for the routine measurement of testosterone, androstenedione, dihydrotestosterone and dehydroepiandrosterone by liquid chromatography tandem mass spectrometry, Annals of Clinical Biochemistry, Sep. 2016, pp. 580-587, vol. 53, issue 5.

Asada et al., 5a-Reductase Type 2 Is Constitutively Expressed int he Dermal Papilla and Connective Tissue Sheath of the Hair Follican In Vivo But Not during Culture in Vitro, The Journal of Clinical Endocrinology and Metabolism, Jun. 2001, pp. 2875-2880, vol. 86 issue 6.

Stellar™ Competent Cells Protocol PT5055-2 Table of contents, Clontech, Accessed Mar. 5, 2018.

Takara Bio Inc., B. subtilis Secretory Protein Expression System, B.subtilis Secretory Protein Expression System, Accessed Mar. 5, 2018.

16S Metagenomic Sequencing Library Preparation: Preparing 16S Ribosomal RNA Gene Amplicons for the Illumina MiSeq System, Illumina, Accessed Mar. 5, 2018.

ONE-Glo™ Luciferase Assay System Technical Manual, Promega, pp. 1-18, Accessed Mar. 5, 2018.

IGEM12_LMU-Munich. Part:BBa_K823003. iGEM Registry of Standart Biological Parts. http://parts.igem.org/Part:BBa_K823003, Accessed Mar. 5, 2018.

5α-Androstan-17β-ol-3-one. Sigma-Aldrich. https://www.sigmaaldrich.com/catalog/product/sigma/a8380?lang=en&region=IL, Accessed Mar. 5, 2018.

Western blot troubleshooting tips. Abcam. http://www.abcam.com/protocols/western-blot-troubleshooting-tips, Accessed Mar. 5, 2018.

Dulbecco's Phosphate Buffered Saline. Biological Industries USA, Inc. http://www.bioind.com/dpbs-no-calcium-no-magnesium-1218/. Accessed Mar. 5, 2018.

Invitrogen, Scientific T. PureLink TM Microbiome DNA Purification Kit. https://www.thermofisher.com/us/en/home/life-science/dna-rna-purification-analysis/dna-extraction/microbiome-dna-extraction.html, Accessed Mar. 5, 2018.

\* cited by examiner

△ - Ligand from type A (Cofactor-NADPH)
○ - Ligand from type B (Hormone-DHT)
▲ - Ligand from type C (Cofactor-NADP)
● - Ligand from type D (Hormone-3adiol)

SEQUENCE LISTING

```
<160> NUMBER OF SEQ ID NOS: 75

<210> SEQ ID NO 1
<211> LENGTH: 322
<212> TYPE: PRT
<213> ORGANISM: Rattus norvegicus

<400> SEQUENCE: 1

Met Asp Ser Ile Ser Leu Arg Val Ala Leu Asn Asp Gly Asn Phe Ile
1               5                   10                  15

Pro Val Leu Gly Phe Gly Thr Thr Val Pro Glu Lys Val Ala Lys Asp
                20                  25                  30

Glu Val Ile Lys Ala Thr Lys Ile Ala Ile Asp Asn Gly Phe Arg His
            35                  40                  45

Phe Asp Ser Ala Tyr Leu Tyr Glu Val Glu Glu Val Gly Gln Ala
    50                  55                  60

Ile Arg Ser Lys Ile Glu Asp Gly Thr Val Lys Arg Glu Asp Ile Phe
65                  70                  75                  80

Tyr Thr Ser Lys Leu Trp Ser Thr Phe His Arg Pro Glu Leu Val Arg
                85                  90                  95

Thr Cys Leu Glu Lys Thr Leu Lys Ser Thr Gln Gln Asp Tyr Val Asp
                100                 105                 110

Leu Tyr Ile Ile His Phe Pro Met Ala Leu Gln Pro Gly Asp Ile Phe
            115                 120                 125

Phe Pro Arg Asp Glu His Gly Lys Leu Leu Phe Glu Thr Val Asp Ile
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Cys Arg Gln Leu Glu Arg Ile
                165                 170                 175

Leu Asn Lys Pro Gly Leu Lys Tyr Lys Pro Val Cys Asn Gln Val Glu
                180                 185                 190

Cys His Leu Tyr Leu Asn Gln Ser Lys Met Leu Asp Tyr Cys Lys Ser
            195                 200                 205

Lys Asp Ile Ile Leu Val Ser Tyr Cys Thr Leu Gly Ser Ser Arg Asp
    210                 215                 220

Lys Thr Trp Val Asp Gln Lys Ser Pro Val Leu Leu Asp Asp Pro Val
225                 230                 235                 240

Leu Cys Ala Ile Ala Lys Lys Tyr Lys Gln Thr Pro Ala Leu Val Ala
                245                 250                 255

Leu Arg Tyr Gln Leu Gln Arg Gly Val Val Pro Leu Ile Arg Ser Phe
                260                 265                 270

Lys Pro Lys Arg Ile Lys Glu Pro Thr Gln Val Phe Glu Phe Gln Leu
            275                 280                 285

Ala Ser Glu Asp Met Lys Ala Leu Asp Gly Leu Asn Arg Asn Phe Arg
    290                 295                 300
```

Tyr Asn Asn Ala Lys Tyr Phe Asp Asp His Pro Asn His Pro Phe Thr
305                 310                 315                 320

Asp Glu

<210> SEQ ID NO 2
<211> LENGTH: 969
<212> TYPE: DNA
<213> ORGANISM: Rattus norvegicus

<400> SEQUENCE: 2

| | | | | | |
|---|---|---|---|---|---|
| atggattcca | tatctctgcg | tgtagcacta | aatgatggta | acttcattcc | tgtactgggg | 60 |
| tttggaacca | ctgtgcctga | aaggttgct | aaggatgaag | ttatcaaggc | tactaaaata | 120 |
| gctatagata | atggattccg | ccattttgac | tctgcttatt | tgtacgaagt | agaagaggaa | 180 |
| gtgggccaag | ccattagaag | caagattgaa | gacggcactg | tgaagagaga | agatatattc | 240 |
| tatacttcaa | agctttggag | cactttccat | agaccagagc | tggtccgaac | ttgcttggaa | 300 |
| aagacactga | aaagcactca | acaggactat | gtggatcttt | atattattca | tttcccaatg | 360 |
| gctttgcagc | ctggagatat | attttttccca | cgagatgagc | atggaaaact | attgtttgaa | 420 |
| acagtggata | tctgtgacac | atgggaggcc | atggaaaagt | gtaaggatgc | aggattggcc | 480 |
| aagtctattg | gggtgtccaa | ctttaactgt | aggcagctgg | agaggattct | gaataagcca | 540 |
| gggctcaaat | acaagcctgt | gtgcaaccag | gtggaatgtc | accttatctc | aaccagagc | 600 |
| aaaatgctgg | actattgtaa | gtcaaaagac | atcattctgg | tttcctactg | cacgctggga | 660 |
| agttcacgag | acaaaacatg | ggtggatcag | aaaagtccag | ttctcctaga | tgatccagtt | 720 |
| ctttgtgcca | tagcaaagaa | gtacaagcaa | accccagccc | tagttgccct | tcgctaccag | 780 |
| cttcagcgtg | gggttgtgcc | cctgatcagg | agtttcaagc | cgaagcggat | caaagagcca | 840 |
| acacaggttt | tgaatttca | gttggcttca | gaggacatga | aagccctgga | tggcttgaac | 900 |
| agaaatttca | gatacaacaa | tgcaaaatat | tttgatgacc | atcccaatca | tccatttact | 960 |
| gatgaatag | | | | | | 969 |

<210> SEQ ID NO 3
<211> LENGTH: 322
<212> TYPE: PRT
<213> ORGANISM: Rattus norvegicus

<400> SEQUENCE: 3

Met Asp Ser Ile Ser Leu Arg Val Ala Leu Asn Asp Gly Asn Phe Ile
1               5                   10                  15

Pro Val Leu Gly Phe Gly Thr Thr Val Pro Glu Lys Val Ala Lys Asp
                20                  25                  30

Glu Val Ile Lys Ala Thr Lys Ile Ala Ile Asp Asn Gly Phe Arg His
            35                  40                  45

Phe Asp Ser Ala Tyr Leu Tyr Glu Val Glu Glu Val Gly Gln Ala
        50                  55                  60

Ile Arg Ser Lys Ile Glu Asp Gly Thr Val Lys Arg Glu Asp Ile Phe
65                  70                  75                  80

Tyr Thr Ser Lys Leu Trp Ser Thr Phe His Arg Pro Glu Leu Val Arg
                85                  90                  95

Thr Cys Leu Glu Lys Thr Leu Lys Ser Thr Gln Leu Asp Tyr Val Asp
                100                 105                 110

Leu Tyr Ile Ile His Phe Pro Met Ala Leu Gln Pro Gly Asp Ile Phe
            115                 120                 125

Phe Pro Arg Asp Glu His Gly Lys Leu Leu Phe Glu Thr Val Asp Ile
            130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Cys Arg Gln Leu Glu Arg Ile
                165                 170                 175

Leu Asn Lys Pro Gly Leu Lys Tyr Lys Pro Val Cys Asn Gln Val Glu
            180                 185                 190

Cys His Leu Tyr Leu Asn Gln Ser Lys Met Leu Asp Tyr Cys Lys Ser
        195                 200                 205

Lys Asp Ile Ile Leu Val Ser Tyr Cys Thr Leu Gly Ser Ser Arg Asp
210                 215                 220

Lys Thr Trp Val Asp Gln Lys Ser Pro Val Leu Leu Asp Asp Pro Val
225                 230                 235                 240

Leu Cys Ala Ile Ala Lys Lys Tyr Lys Gln Thr Pro Ala Leu Val Ala
                245                 250                 255

Leu Arg Tyr Gln Leu Gln Arg Gly Val Val Pro Leu Ile Arg Ser Phe
            260                 265                 270

Asn Ala Lys Arg Ile Lys Glu Leu Thr Gln Val Phe Glu Phe Gln Leu
        275                 280                 285

Ala Ser Glu Asp Met Lys Ala Leu Asp Gly Leu Asn Arg Asn Phe Arg
290                 295                 300

Tyr Asn Asn Ala Lys Tyr Phe Asp Asp His Pro Asn His Pro Phe Thr
305                 310                 315                 320

Asp Glu

<210> SEQ ID NO 4
<211> LENGTH: 969
<212> TYPE: DNA
<213> ORGANISM: Rattus norvegicus

<400> SEQUENCE: 4
atggattcca tatctctgcg tgtagcacta aatgatggta acttcattcc tgtactgggg      60
tttggaacca ctgtgcctga aaggttgct aaggatgaag ttatcaaggc tactaaaata     120
gctatagata tggattccg ccattttgac tctgcttatt tgtacgaagt agaagaggaa     180
gtgggccaag ccattagaag caagattgaa acggcactg tgaagagaga agatatattc     240
tatacttcaa gctttggag cactttccat agaccagagc tggtccgaac ttgcttggaa     300
aagcacctga aaagcactca actggactat gtggatcttt atattattca tttcccaatg     360
gctttgcagc ctggagatat atttttccca cgagatgagc atggaaaact attgtttgaa     420
acagtggata tctgtgacac atgggaggcc atggagaagt gtaaggatgc aggattggcc     480
aagtctattg ggtgtccaa ctttaactgc aggcagctgg agaggattct gaataagcca     540
gggctcaaat acaagcctgt gtgcaaccag gtggaatgtc acctttatct caaccagagc     600
aaaatgctgg actattgtaa gtcaaaagac atcattctgg tttcctactg cacgctggga     660
agttcacgag acaaaacatg ggtggatcag aaaagtccag ttctcctaga tgatccagtt     720
ctttgtgcca tagcaaagaa gtacaagcaa accccagccc tagttgccct tcgctaccag     780
ctgcagcgtg gggttgtgcc cctgatcagg agtttcaacg cgaagcggat caagagcta     840 acacaggttt ttgaattcca gttggcttca gaggacatga aagccctgga tggcttgaac     900
agaaatttca gatacaacaa tgcaaaatat tttgatgacc atcccaatca tccatttact     960
gatgaatag                                                                969

<210> SEQ ID NO 5
<211> LENGTH: 29
<212> TYPE: PRT
<213> ORGANISM: Bacillus subtilis

<400> SEQUENCE: 5

Met Arg Ser Lys Lys Leu Trp Ile Ser Leu Leu Phe Ala Leu Thr Leu
1               5                   10                  15

Ile Phe Thr Met Ala Phe Ser Asn Met Ser Val Gln Ala
            20                  25

<210> SEQ ID NO 6
<211> LENGTH: 87
<212> TYPE: DNA
<213> ORGANISM: Bacillus subtilis

<400> SEQUENCE: 6
atgcgttcaa aaaactttg gatctctctt cttttcgctc ttacacttat cttcacaatg    60
gctttctcaa acatgtctgt tcaagcg                                       87

<210> SEQ ID NO 7
<211> LENGTH: 350
<212> TYPE: PRT
<213> ORGANISM: Artificial
<220> FEATURE:
<223> OTHER INFORMATION: Synthetic

<400> SEQUENCE: 7

Met Arg Ser Lys Lys Leu Trp Ile Ser Leu Leu Phe Ala Leu Thr Leu
1               5                   10                  15

Ile Phe Thr Met Ala Phe Ser Asn Met Ser Val Gln Ala Met Asp Ser
            20                  25                  30

Ile Ser Leu Arg Val Ala Leu Asn Asp Gly Asn Phe Ile Pro Val Leu
        35                  40                  45

Gly Phe Gly Thr Thr Val Pro Glu Lys Val Ala Lys Asp Glu Val Ile
    50                  55                  60

Lys Ala Lys Ile Ala Ile Asp Asn Gly Phe Arg His Phe Asp Ser Ala
65                  70                  75                  80

Tyr Leu Tyr Glu Val Glu Glu Val Gly Gln Ala Ile Arg Ser Lys
                85                  90                  95

Ile Glu Asp Gly Thr Val Lys Arg Glu Asp Ile Phe Tyr Thr Ser Lys
            100                 105                 110

Leu Trp Ser Thr Phe His Arg Pro Glu Leu Val Arg Thr Cys Leu Glu
        115                 120                 125

Lys Thr Leu Lys Ser Thr Gln Gln Asp Tyr Val Asp Leu Tyr Ile Ile
    130                 135                 140

His Phe Pro Met Ala Leu Gln Pro Gly Asp Ile Phe Pro Arg Asp
145                 150                 155                 160

Glu His Gly Lys Leu Leu Phe Glu Thr Val Asp Ile Cys Asp Thr Trp
                165                 170                 175

Glu Ala Met Glu Lys Cys Lys Asp Ala Gly Leu Ala Lys Ser Ile Gly
            180                 185                 190

Val Ser Asn Phe Asn Cys Arg Gln Leu Glu Arg Ile Leu Asn Lys Pro
        195                 200                 205

Gly Leu Lys Tyr Lys Pro Val Cys Asn Gln Val Glu Cys His Leu Tyr
    210                 215                 220

```
Leu Asn Gln Ser Lys Met Leu Asp Tyr Cys Lys Ser Lys Asp Ile Ile
225                 230                 235                 240

Leu Val Ser Tyr Cys Thr Leu Gly Ser Ser Arg Asp Lys Thr Trp Val
            245                 250                 255

Asp Gln Lys Ser Pro Val Leu Leu Asp Asp Pro Val Leu Cys Ala Ile
        260                 265                 270

Ala Lys Lys Tyr Lys Gln Thr Pro Ala Leu Val Ala Leu Arg Tyr Gln
    275                 280                 285

Leu Gln Arg Gly Val Val Pro Leu Ile Arg Ser Phe Lys Pro Lys Arg
290                 295                 300

Ile Lys Glu Pro Thr Gln Val Phe Glu Phe Gln Leu Ala Ser Glu Asp
305                 310                 315                 320

Met Lys Ala Leu Asp Gly Leu Asn Arg Asn Phe Arg Tyr Asn Asn Ala
                325                 330                 335

Lys Tyr Phe Asp Asp His Pro Asn His Pro Phe Thr Asp Glu
            340                 345                 350

<210> SEQ ID NO 8
<211> LENGTH: 1056
<212> TYPE: DNA
<213> ORGANISM: Artificial
<220> FEATURE:
<223> OTHER INFORMATION: Synthetic

<400> SEQUENCE: 8
atgcgttcaa aaaactttg  gatctctctt cttttcgctc ttacacttat cttcacaatg      60
gctttctcaa acatgtctgt tcaagcgatg gattccatat ctctgcgtgt agcactaaat     120
gatggtaact tcattcctgt actggggttt ggaaccactg tgcctgagaa ggttgctaag     180
gatgaagtta tcaaggctac taaaatagct atagataatg gattccgcca ttttgactct     240
gcttatttgt acgaagtaga gaggaagtg  ggccaagcca ttagaagcaa gattgaagac     300
ggcactgtga agagagaaga tatattctat acttcaaagc tttggagcac tttccataga     360
ccagagctgg tccgaacttg cttggaaaag acactgaaaa gcactcaaca ggactatgtg     420
gatctttata ttattcattt cccaatggct ttgcagcctg gagatatatt tttcccacga     480
gatgagcatg aaaactatt  gtttgaaaca gtggatatct gtgacacatg ggaggccatg     540
gaaaagtgta aggatgcagg attggccaag tctattgggg tgtccaactt taactgtagg     600
cagctggaga ggattctgaa taagccaggg ctcaaataca gcctgtgtg  caaccaggtg     660 gaatgtcacc tttatctcaa ccagagcaaa atgctggact attgtaagtc aaaagacatc     720
attctggttt cctactgcac gctgggaagt tcacgagaca aacatgggt  ggatcagaaa     780 agtccagttc tcctagatga tccagttctt tgtgccatag caagaagta  caagcaaacc     840 ccagccctag ttgcccttcg ctaccagctt cagcgtgggg ttgtgcccct gatcaggagt     900
ttcaagccga gcggatcaa  agagccaaca caggttttg  aatttcagtt ggcttcagag     960
gacatgaaag ccctggatgg cttgaacaga aatttcagat acaacaatgc aaaatatttt    1020
gatgaccatc ccaatcatcc atttactgat gaatag                              1056

<210> SEQ ID NO 9
<211> LENGTH: 491
<212> TYPE: PRT
<213> ORGANISM: Escherichia coli

<400> SEQUENCE: 9
```

```
Met Ala Val Thr Gln Thr Ala Gln Ala Cys Asp Leu Val Ile Phe Gly
1               5                   10                  15
Ala Lys Gly Asp Leu Ala Arg Arg Lys Leu Leu Pro Ser Leu Tyr Gln
            20                  25                  30
Leu Glu Lys Ala Gly Gln Leu Asn Pro Asp Thr Arg Ile Ile Gly Val
            35                  40                  45
Gly Arg Ala Asp Trp Asp Lys Ala Ala Tyr Thr Lys Val Val Arg Glu
        50                  55                  60
Ala Leu Glu Thr Phe Met Lys Glu Thr Ile Asp Glu Gly Leu Trp Asp
65                  70                  75                  80
Thr Leu Ser Ala Arg Leu Asp Phe Cys Asn Leu Asp Val Asn Asp Thr
                85                  90                  95
Ala Ala Phe Ser Arg Leu Gly Ala Met Leu Asp Gln Lys Asn Arg Ile
            100                 105                 110
Thr Ile Asn Tyr Phe Ala Met Pro Pro Ser Thr Phe Gly Ala Ile Cys
            115                 120                 125
Lys Gly Leu Gly Glu Ala Lys Leu Asn Ala Lys Pro Ala Arg Val Val
        130                 135                 140
Met Glu Lys Pro Leu Gly Thr Ser Leu Ala Thr Ser Gln Glu Ile Asn
145                 150                 155                 160
Asp Gln Val Gly Glu Tyr Phe Glu Glu Cys Gln Val Tyr Arg Ile Asp
                165                 170                 175
His Tyr Leu Gly Lys Glu Thr Val Leu Asn Leu Leu Ala Leu Arg Phe
            180                 185                 190
Ala Asn Ser Leu Phe Val Asn Asn Trp Asp Asn Arg Thr Ile Asp His
            195                 200                 205
Val Glu Ile Thr Val Ala Glu Glu Val Gly Ile Glu Gly Arg Trp Gly
        210                 215                 220
Tyr Phe Asp Lys Ala Gly Gln Met Arg Asp Met Ile Gln Asn His Leu
225                 230                 235                 240
Leu Gln Ile Leu Cys Met Ile Ala Met Ser Pro Pro Ser Asp Leu Ser
                245                 250                 255
Ala Asp Ser Ile Arg Asp Glu Lys Val Lys Val Leu Lys Ser Leu Arg
            260                 265                 270
Arg Ile Asp Arg Ser Asn Val Arg Glu Lys Thr Val Arg Gly Gln Tyr
            275                 280                 285
Thr Ala Gly Phe Ala Gln Gly Lys Lys Val Pro Gly Tyr Leu Glu Glu
        290                 295                 300
Glu Gly Ala Asn Lys Ser Ser Asn Thr Glu Thr Phe Val Ala Ile Arg
305                 310                 315                 320
Val Asp Ile Asp Asn Trp Arg Trp Ala Gly Val Pro Phe Tyr Leu Arg
                325                 330                 335
Thr Gly Lys Arg Leu Pro Thr Lys Cys Ser Glu Val Val Tyr Phe
            340                 345                 350
Lys Thr Pro Glu Leu Asn Leu Phe Lys Glu Ser Trp Gln Asp Leu Pro
            355                 360                 365
Gln Asn Lys Leu Thr Ile Arg Leu Gln Pro Asp Glu Gly Val Asp Ile
        370                 375                 380
Gln Val Leu Asn Lys Val Pro Gly Leu Asp His Lys His Asn Leu Gln
385                 390                 395                 400
Ile Thr Lys Leu Asp Leu Ser Tyr Ser Glu Thr Phe Asn Gln Thr His
                405                 410                 415
Leu Ala Asp Ala Tyr Glu Arg Leu Leu Leu Glu Thr Met Arg Gly Ile
```

```
                    420                 425                 430
Gln Ala Leu Phe Val Arg Arg Asp Glu Val Glu Ala Trp Lys Trp
                435                 440                 445
Val Asp Ser Ile Thr Glu Ala Trp Ala Met Asp Asn Asp Ala Pro Lys
                450                 455                 460
Pro Tyr Gln Ala Gly Thr Trp Gly Pro Val Ala Ser Val Ala Met Ile
465                 470                 475                 480
Thr Arg Asp Gly Arg Ser Trp Asn Glu Phe Glu
                485                 490

<210> SEQ ID NO 10
<211> LENGTH: 30
<212> TYPE: PRT
<213> ORGANISM: Bacillus subtilis

<400> SEQUENCE: 10

Met Lys Lys Asn Thr Leu Leu Lys Val Gly Leu Cys Val Ser Leu Leu
1               5                   10                  15

Gly Thr Thr Gln Phe Val Ser Thr Ile Ser Ser Val Gln Ala
            20                  25                  30

<210> SEQ ID NO 11
<211> LENGTH: 17
<212> TYPE: PRT
<213> ORGANISM: Bacillus subtilis

<400> SEQUENCE: 11

Met Lys Leu Ala Ala Cys Phe Leu Thr Leu Leu Pro Gly Phe Ala Val
1               5                   10                  15

Ala

<210> SEQ ID NO 12
<211> LENGTH: 29
<212> TYPE: PRT
<213> ORGANISM: Bacillus subtilis

<400> SEQUENCE: 12

Met Asn Asp Leu Asn Asp Phe Leu Lys Thr Ile Leu Leu Ser Phe Ile
1               5                   10                  15

Phe Phe Leu Leu Leu Ser Leu Pro Thr Val Ala Glu Ala
            20                  25

<210> SEQ ID NO 13
<211> LENGTH: 21
<212> TYPE: PRT
<213> ORGANISM: Bacillus subtilis

<400> SEQUENCE: 13

Met Lys Lys Leu Ala Ile Met Ala Ala Ala Ser Met Val Phe Ala Val
1               5                   10                  15

Ser Ser Ala His Ala
            20

<210> SEQ ID NO 14
<211> LENGTH: 23
<212> TYPE: PRT
<213> ORGANISM: Bacillus subtilis

<400> SEQUENCE: 14

Met Lys Leu Lys Phe Ile Ser Met Ala Val Phe Ser Ala Leu Thr Leu
1               5                   10                  15
```

```
Gly Val Ala Thr Asn Ala Ser
            20

<210> SEQ ID NO 15
<211> LENGTH: 20
<212> TYPE: PRT
<213> ORGANISM: Bacillus subtilis

<400> SEQUENCE: 15

Met Arg Thr Leu Gln Gly Trp Leu Leu Pro Val Phe Met Leu Pro Met
1               5                   10                  15

Ala Val Tyr Ala
            20

<210> SEQ ID NO 16
<211> LENGTH: 29
<212> TYPE: PRT
<213> ORGANISM: Bacillus subtilis

<400> SEQUENCE: 16

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 17
<211> LENGTH: 28
<212> TYPE: PRT
<213> ORGANISM: Bacillus subtilis

<400> SEQUENCE: 17

Met Leu Lys Lys Val Ile Leu Ala Ala Phe Ile Leu Val Gly Ser Thr
1               5                   10                  15

Leu Gly Ala Phe Ser Phe Ser Ser Asp Ala Ser Ala
            20                  25

<210> SEQ ID NO 18
<211> LENGTH: 29
<212> TYPE: PRT
<213> ORGANISM: Bacillus subtilis

<400> SEQUENCE: 18

Met Lys Lys Lys Gln Val Met Leu Ala Leu Thr Ala Ala Ala Gly Leu
1               5                   10                  15

Gly Leu Thr Ala Leu His Ser Pro Ala Ala Lys Ala
            20                  25

<210> SEQ ID NO 19
<211> LENGTH: 26
<212> TYPE: PRT
<213> ORGANISM: Bacillus subtilis

<400> SEQUENCE: 19

Met Lys Lys Glu Leu Leu Ala Ser Leu Val Leu Cys Leu Ser Leu Ser
1               5                   10                  15

Pro Leu Val Ser Thr Asn Glu Val Phe Ala
            20                  25

<210> SEQ ID NO 20
<211> LENGTH: 28
<212> TYPE: PRT
<213> ORGANISM: Bacillus subtilis
```

```
<400> SEQUENCE: 20

Met Thr Lys Lys Ala Trp Phe Leu Pro Leu Val Cys Val Leu Leu Ile
1               5                   10                  15

Ser Gly Trp Leu Ala Pro Ala Ala Ser Ala Ser Ala
            20                  25

<210> SEQ ID NO 21
<211> LENGTH: 36
<212> TYPE: PRT
<213> ORGANISM: Bacillus subtilis

<400> SEQUENCE: 21

Met Lys Leu Lys Thr Lys Ala Ser Ile Lys Phe Gly Ile Cys Val Gly
1               5                   10                  15

Leu Leu Cys Leu Ser Ile Thr Gly Phe Thr Pro Phe Phe Asn Ser Thr
            20                  25                  30

His Ala Glu Ala
        35

<210> SEQ ID NO 22
<211> LENGTH: 26
<212> TYPE: PRT
<213> ORGANISM: Bacillus subtilis

<400> SEQUENCE: 22

Met Lys Lys Ala Phe Ile Leu Ser Ala Ala Ala Val Gly Leu Phe
1               5                   10                  15

Thr Phe Gly Gly Val Gln Gln Ala Ser Ala
            20                  25

<210> SEQ ID NO 23
<211> LENGTH: 26
<212> TYPE: PRT
<213> ORGANISM: Bacillus subtilis

<400> SEQUENCE: 23

Met Met Lys Lys Leu Phe His Ser Thr Leu Ile Val Leu Leu Phe Phe
1               5                   10                  15

Ser Phe Phe Gly Val Gln Pro Ile His Ala
            20                  25

<210> SEQ ID NO 24
<211> LENGTH: 27
<212> TYPE: PRT
<213> ORGANISM: Bacillus subtilis

<400> SEQUENCE: 24

Met Gly Met Lys Lys Lys Leu Ser Leu Gly Val Ala Ser Ala Ala Leu
1               5                   10                  15

Gly Leu Ala Leu Val Gly Gly Gly Thr Trp Ala
            20                  25

<210> SEQ ID NO 25
<211> LENGTH: 31
<212> TYPE: PRT
<213> ORGANISM: Bacillus subtilis

<400> SEQUENCE: 25

Met Lys Ser Lys Gly Ser Ile Met Ala Cys Leu Ile Leu Phe Ser Phe
1               5                   10                  15
```

```
Thr Ile Thr Thr Phe Ile Asn Thr Glu Thr Ile Ser Ala Phe Ser
            20                  25                  30

<210> SEQ ID NO 26
<211> LENGTH: 32
<212> TYPE: PRT
<213> ORGANISM: Bacillus subtilis

<400> SEQUENCE: 26

Met Lys Lys Lys Arg Arg Asn Phe Lys Arg Phe Ile Ala Ala Phe
1               5                   10                  15

Leu Val Leu Ala Leu Met Ile Ser Leu Val Pro Ala Asp Val Leu Ala
            20                  25                  30

<210> SEQ ID NO 27
<211> LENGTH: 23
<212> TYPE: PRT
<213> ORGANISM: Bacillus subtilis

<400> SEQUENCE: 27

Met Asn Gln Met Lys Asp Thr Ile Leu Leu Ala Gly Leu Gly Leu Ile
1               5                   10                  15

Gly Gly Ser Ile Ala Leu Ala
            20

<210> SEQ ID NO 28
<211> LENGTH: 28
<212> TYPE: PRT
<213> ORGANISM: Bacillus subtilis

<400> SEQUENCE: 28

Met Asp Lys Phe Leu Asn Asn Arg Trp Ala Val Lys Ile Ile Ala Leu
1               5                   10                  15

Leu Phe Ala Leu Leu Leu Tyr Val Ala Val Asn Ser
            20                  25

<210> SEQ ID NO 29
<211> LENGTH: 34
<212> TYPE: PRT
<213> ORGANISM: Bacillus subtilis

<400> SEQUENCE: 29

Met Lys Lys Lys Thr Lys Ile Ile Leu Ser Leu Leu Ala Ala Leu Ile
1               5                   10                  15

Val Ile Leu Ile Val Leu Pro Val Leu Ser Pro Val Val Phe Thr Ala
            20                  25                  30

Ser Ser

<210> SEQ ID NO 30
<211> LENGTH: 25
<212> TYPE: PRT
<213> ORGANISM: Bacillus subtilis

<400> SEQUENCE: 30

Met Lys Lys Arg Leu Ile Gly Phe Leu Val Leu Val Pro Ala Leu Ile
1               5                   10                  15

Met Ser Gly Ile Thr Leu Ile Glu Ala
            20                  25

<210> SEQ ID NO 31
<211> LENGTH: 28
<212> TYPE: PRT
```

<213> ORGANISM: Bacillus subtilis

<400> SEQUENCE: 31

Met Lys Arg Leu Phe Met Lys Ala Ser Leu Val Leu Phe Ala Val Val
1               5                   10                  15

Phe Val Phe Ala Val Lys Gly Ala Pro Ala Lys Ala
            20                  25

<210> SEQ ID NO 32
<211> LENGTH: 24
<212> TYPE: PRT
<213> ORGANISM: Bacillus subtilis

<400> SEQUENCE: 32

Met Lys Lys Arg Leu Ile Gln Val Met Ile Met Phe Thr Leu Leu Leu
1               5                   10                  15

Thr Met Ala Phe Ser Ala Asp Ala
            20

<210> SEQ ID NO 33
<211> LENGTH: 37
<212> TYPE: PRT
<213> ORGANISM: Bacillus subtilis

<400> SEQUENCE: 33

Met Ser Gly Lys Lys Lys Glu Ser Gly Lys Phe Arg Ser Val Leu Leu
1               5                   10                  15

Ile Ile Ile Leu Pro Leu Met Phe Leu Leu Ile Ala Gly Gly Ile Val
            20                  25                  30

Leu Trp Ala Ala Gly
        35

<210> SEQ ID NO 34
<211> LENGTH: 22
<212> TYPE: PRT
<213> ORGANISM: Bacillus subtilis

<400> SEQUENCE: 34

Met Lys Lys Arg Phe Phe Gly Pro Ile Ile Leu Ala Phe Ile Leu Phe
1               5                   10                  15

Ala Gly Ala Ile Ala Ala
            20

<210> SEQ ID NO 35
<211> LENGTH: 21
<212> TYPE: PRT
<213> ORGANISM: Bacillus subtilis

<400> SEQUENCE: 35

Met Phe Lys Lys His Thr Ile Ser Leu Leu Ile Phe Leu Leu Ala
1               5                   10                  15

Ser Ala Val Leu Ala
            20

<210> SEQ ID NO 36
<211> LENGTH: 34
<212> TYPE: PRT
<213> ORGANISM: Bacillus subtilis

<400> SEQUENCE: 36

Met Lys Lys Ile Val Ala Ala Ile Val Val Ile Gly Leu Val Phe Ile
1               5                   10                  15

Ala Phe Phe Tyr Leu Tyr Ser Arg Ser Gly Asp Val Tyr Gln Ser Val
            20                  25                  30

Asp Ala

<210> SEQ ID NO 37
<211> LENGTH: 32
<212> TYPE: PRT
<213> ORGANISM: Bacillus subtilis

<400> SEQUENCE: 37

Met Lys Lys Phe Pro Lys Lys Leu Leu Pro Ile Ala Val Leu Ser Ser
1               5                   10                  15

Ile Ala Phe Ser Ser Leu Ala Ser Gly Ser Val Pro Glu Ala Ser Ala
            20                  25                  30

<210> SEQ ID NO 38
<211> LENGTH: 25
<212> TYPE: PRT
<213> ORGANISM: Bacillus subtilis

<400> SEQUENCE: 38

Met Arg Phe Thr Lys Val Val Gly Phe Leu Ser Val Leu Gly Leu Ala
1               5                   10                  15

Ala Val Phe Pro Leu Thr Ala Gln Ala
            20                  25

<210> SEQ ID NO 39
<211> LENGTH: 35
<212> TYPE: PRT
<213> ORGANISM: Bacillus subtilis

<400> SEQUENCE: 39

Met Arg Ile Gln Lys Arg Arg Thr His Val Glu Asn Ile Leu Arg Ile
1               5                   10                  15

Leu Leu Pro Pro Ile Met Ile Leu Ser Leu Ile Leu Pro Thr Pro Pro
            20                  25                  30

Ile His Ala
        35

<210> SEQ ID NO 40
<211> LENGTH: 34
<212> TYPE: PRT
<213> ORGANISM: Bacillus subtilis

<400> SEQUENCE: 40

Met Ile Lys Met Gln Lys Lys Asn Lys Phe Met Asn Arg Gly Ala Ala
1               5                   10                  15

Ile Leu Ser Ile Cys Phe Ala Leu Phe Phe Asp Ile Leu Gly Arg
            20                  25                  30

Met Ala

<210> SEQ ID NO 41
<211> LENGTH: 29
<212> TYPE: PRT
<213> ORGANISM: Bacillus subtilis

<400> SEQUENCE: 41

Met Asn Ile Lys Lys Phe Ala Lys Gln Ala Thr Val Leu Thr Phe Thr
1               5                   10                  15

Thr Ala Leu Leu Ala Gly Gly Ala Thr Gln Ala Phe Ala

<210> SEQ ID NO 42
<211> LENGTH: 24
<212> TYPE: PRT
<213> ORGANISM: Bacillus subtilis

<400> SEQUENCE: 42

Met Lys Leu Lys Ser Lys Leu Leu Ser Cys Leu Ala Leu Ser Thr
1               5                   10                  15

Val Phe Val Ala Thr Thr Ile Ala
            20

<210> SEQ ID NO 43
<211> LENGTH: 26
<212> TYPE: PRT
<213> ORGANISM: Bacillus subtilis

<400> SEQUENCE: 43

Met Leu Thr Lys Arg Leu Leu Thr Ile Tyr Ile Met Leu Leu Gly Leu
1               5                   10                  15

Ile Ala Trp Phe Pro Gly Ala Ala Gln Ala
            20                  25

<210> SEQ ID NO 44
<211> LENGTH: 33
<212> TYPE: PRT
<213> ORGANISM: Bacillus subtilis

<400> SEQUENCE: 44

Met Lys Leu Phe Asn Arg Lys Val Thr Leu Val Ser Leu Ile Leu Met
1               5                   10                  15

Ala Val Phe Gln Phe Phe Met Ala Leu Ile Ile Lys Arg Ile Val Ile
            20                  25                  30

Ser

<210> SEQ ID NO 45
<211> LENGTH: 19
<212> TYPE: PRT
<213> ORGANISM: Bacillus subtilis

<400> SEQUENCE: 45

Met Lys Lys Leu Val Leu Cys Val Ser Ile Leu Ala Val Ile Leu Ser
1               5                   10                  15

Gly Val Ala

<210> SEQ ID NO 46
<211> LENGTH: 87
<212> TYPE: DNA
<213> ORGANISM: Bacillus subtilis

<400> SEQUENCE: 46
gtgagaagca aaaaattgtg gatcagcttg ttgtttgcgt taacgttaat ctttacgatg    60
gcgttcagca acatgtctgc gcaggct                                       87

<210> SEQ ID NO 47
<211> LENGTH: 84
<212> TYPE: DNA
<213> ORGANISM: Bacillus subtilis

<400> SEQUENCE: 47

```
atgttgaaga aagtcatttt agccgctttt atcttagtag gaagtacttt gggagctttt    60
agtttttcat cagatgccag tgcg                                          84
```

<210> SEQ ID NO 48
<211> LENGTH: 87
<212> TYPE: DNA
<213> ORGANISM: Bacillus subtilis

<400> SEQUENCE: 48

```
atgaaaaaga aacaagtaat gctcgcttta acagctgccg caggactggg tttgacagca    60
cttcattccg ctcccgcagc aaaagct                                       87
```

<210> SEQ ID NO 49
<211> LENGTH: 78
<212> TYPE: DNA
<213> ORGANISM: Bacillus subtilis

<400> SEQUENCE: 49

```
atgaaaaaag aattacttgc ttcactagtt ttatgtctat cattgtcacc attagtgtca    60
acaaatgaag ttttgca                                                  78
```

<210> SEQ ID NO 50
<211> LENGTH: 84
<212> TYPE: DNA
<213> ORGANISM: Bacillus subtilis

<400> SEQUENCE: 50

```
atgacaaaaa aagcatggtt tctgccgctc gtctgtgtat tactgatttc cggatggctt    60
gcgccagcag cttcagcaag cgcg                                          84
```

<210> SEQ ID NO 51
<211> LENGTH: 108
<212> TYPE: DNA
<213> ORGANISM: Bacillus subtilis

<400> SEQUENCE: 51

```
atgaagttga aaactaaagc gtcaataaaa ttcggaatat gtgttgggct tttatgttta    60
agcattactg gtttcacacc ttttttcaac tcaacacatg ccgaagca               108
```

<210> SEQ ID NO 52
<211> LENGTH: 78
<212> TYPE: DNA
<213> ORGANISM: Bacillus subtilis

<400> SEQUENCE: 52

```
atgaagaaag catttatttt atctgctgcc gctgcggttg gattattcac attcggggc    60 gtacagcaag catcagcg                                                 78
```

<210> SEQ ID NO 53
<211> LENGTH: 78
<212> TYPE: DNA
<213> ORGANISM: Bacillus subtilis

<400> SEQUENCE: 53

```
atgatgaaaa agctatttca ttccacactt attgtgttgt tattctttag ttttttcggc    60
gttcagccca tccacgcg                                                 78
```

<210> SEQ ID NO 54
<211> LENGTH: 81

<212> TYPE: DNA
<213> ORGANISM: Bacillus subtilis

<400> SEQUENCE: 54
atgggtatga aaagaaatt gagtttagga gttgcttctg cagcactagg attagcttta      60
gttggaggag aacatgggc a                                                81

<210> SEQ ID NO 55
<211> LENGTH: 93
<212> TYPE: DNA
<213> ORGANISM: Bacillus subtilis

<400> SEQUENCE: 55
atgaagtcca aggatcgat tatggcatgt ctcatccttt tttcctttac aataacgacg      60
tttattaata ctgaaacgat ctctgccttt tcg                                  93

<210> SEQ ID NO 56
<211> LENGTH: 96
<212> TYPE: DNA
<213> ORGANISM: Bacillus subtilis

<400> SEQUENCE: 56
atgaaaaaaa aaaaaaggcg aaactttaaa aggttcattg cagcattttt agtgttggct      60
ttaatgattt cattagtgcc agccgatgta ctagca                                96

<210> SEQ ID NO 57
<211> LENGTH: 69
<212> TYPE: DNA
<213> ORGANISM: Bacillus subtilis

<400> SEQUENCE: 57
atgaatcaaa tgaaagatac aatattgctc gccggtctcg gattgatagg cggttcgatt      60
gccctagcc                                                             69

<210> SEQ ID NO 58
<211> LENGTH: 84
<212> TYPE: DNA
<213> ORGANISM: Bacillus subtilis

<400> SEQUENCE: 58
atggataaat tcttaaacaa ccgctgggct gtgaaaatta ttgctctgct tttcgcgctc      60
ttgctttatg tggcggttaa cagc                                            84

<210> SEQ ID NO 59
<211> LENGTH: 102
<212> TYPE: DNA
<213> ORGANISM: Bacillus subtilis

<400> SEQUENCE: 59
atgaaaaaga aaactaaaat tatactttct ctcttggcag cacttattgt tatattgata      60
gtacttccag ttctatctcc tgttgtcttt acagcttctt cg                        102

<210> SEQ ID NO 60
<211> LENGTH: 75
<212> TYPE: DNA
<213> ORGANISM: Bacillus subtilis

<400> SEQUENCE: 60
atgaagaaga ggctaatcgg attttttggtc ttagttcctg ctttgattat gtcaggtatt    60
actttaatcg aagca                                                          75

<210> SEQ ID NO 61
<211> LENGTH: 84
<212> TYPE: DNA
<213> ORGANISM: Bacillus subtilis

<400> SEQUENCE: 61
atgaaaagac tgtttatgaa ggcttcattg gtgttattcg cagtagtatt tgtttttgcc        60
gtcaaaggtg cacccgccaa ggcg                                                84

<210> SEQ ID NO 62
<211> LENGTH: 72
<212> TYPE: DNA
<213> ORGANISM: Bacillus subtilis

<400> SEQUENCE: 62
atgaaaaaga gactgattca agtcatgatc atgttcaccc tgctgttgac tatggcattt        60
tcggcagatg ca                                                             72

<210> SEQ ID NO 63
<211> LENGTH: 111
<212> TYPE: DNA
<213> ORGANISM: Bacillus subtilis

<400> SEQUENCE: 63
atgtccggca aaagaaaga atcaggtaag ttccgttcgg ttttgcttat cattatcctc          60
ccgctgatgt ttctattaat cgcagggggg attgttcttt gggctgctgg t                 111

<210> SEQ ID NO 64
<211> LENGTH: 66
<212> TYPE: DNA
<213> ORGANISM: Bacillus subtilis

<400> SEQUENCE: 64
atgaaaaagc gttttttcgg tccaattatt ttggcgttta ttctattcgc aggcgccatc         60
gcagcg                                                                    66

<210> SEQ ID NO 65
<211> LENGTH: 63
<212> TYPE: DNA
<213> ORGANISM: Bacillus subtilis

<400> SEQUENCE: 65
atgtttaaga aacatacgat ctctttgctc attatatttt tacttgcgtc tgctgtttta         60
gca                                                                       63

<210> SEQ ID NO 66
<211> LENGTH: 102
<212> TYPE: DNA
<213> ORGANISM: Bacillus subtilis

<400> SEQUENCE: 66
atgaaaaaaa tagtggcagc catcgtggta atcggtcttg tgtttatcgc atttttttat         60
ctttacagcc gatcaggcga tgtgtatcaa tcggtagacg cg                           102

<210> SEQ ID NO 67
<211> LENGTH: 96
<212> TYPE: DNA
<213> ORGANISM: Bacillus subtilis

```
<400> SEQUENCE: 67
atgaaaaaat tcccgaagaa attactgcct atcgcggttt tatcatcaat tgcgttcagc      60
agcttagcca gcggcagtgt gcctgaagcc agcgcc                                96

<210> SEQ ID NO 68
<211> LENGTH: 75
<212> TYPE: DNA
<213> ORGANISM: Bacillus subtilis

<400> SEQUENCE: 68
atgagattca ctaaggtagt tggattttg tctgttttag ggttggctgc ggttttcca      60 ttaacggcac aagca                                                       75

<210> SEQ ID NO 69
<211> LENGTH: 105
<212> TYPE: DNA
<213> ORGANISM: Bacillus subtilis

<400> SEQUENCE: 69
atgagaatac agaaaagacg aacacacgtc gaaaacattc tccgtattct tttgccccca      60
attatgatac ttagcctaat cctcccaaca ccacccattc atgca                     105

<210> SEQ ID NO 70
<211> LENGTH: 102
<212> TYPE: DNA
<213> ORGANISM: Bacillus subtilis

<400> SEQUENCE: 70
atgattaaaa tgcaaaaaaa gaataaattt atgaatagag gagcagcgat tctaagtatt      60
tgtttcgctc tcttttttctt tgacatcctg gggagaatgg ca                       102

<210> SEQ ID NO 71
<211> LENGTH: 87
<212> TYPE: DNA
<213> ORGANISM: Bacillus subtilis

<400> SEQUENCE: 71
atgaacatca aaagtttgc aaaacaagca acagtattaa cctttactac cgcactgctg      60
gcaggaggcg caactcaagc gtttgcg                                          87

<210> SEQ ID NO 72
<211> LENGTH: 72
<212> TYPE: DNA
<213> ORGANISM: Bacillus subtilis

<400> SEQUENCE: 72
atgaaattga agtctaaact attactctct tgtctggctc taagcactgt gttcgtggca      60
acaactattg cc                                                          72

<210> SEQ ID NO 73
<211> LENGTH: 78
<212> TYPE: DNA
<213> ORGANISM: Bacillus subtilis

<400> SEQUENCE: 73
atgttgacga agcgcttgct tactatatac attatgttat tagggttgat tgcatggttt      60
ccaggtgcgg cacaagct                                                    78
```

```
<210> SEQ ID NO 74
<211> LENGTH: 99
<212> TYPE: DNA
<213> ORGANISM: Bacillus subtilis

<400> SEQUENCE: 74
atgaaacttt ttaatcggaa ggtcactttg gtttctctta tcctgatggc tgtctttcaa      60
ttcttcatgg cattgatcat taaacggatt gtcatcagt                             99

<210> SEQ ID NO 75
<211> LENGTH: 57
<212> TYPE: DNA
<213> ORGANISM: Bacillus subtilis

<400> SEQUENCE: 75
atgaaaaaac ttgtgctttg cgtatctatt ttagctgtga ttttaagtgg agtagct         57
```

COMPOSITION AND METHOD FOR TREATING ANDROGEN-DEPENDENT DISORDERS

CROSS REFERENCE TO RELATED APPLICATIONS

This application claims priority to U.S. Provisional Patent Application No. 62/313,996, filed Mar. 28, 2016, and to U.S. Provisional Patent Application No. 62/396,167, filed Sep. 18, 2016, the contents of which are incorporated herein by reference in their entirety.

FIELD OF INVENTION

This invention is directed to microorganisms capable of expressing and secreting a dihydrotestosterone (DHT) reductase and uses thereof, such as for treatment of androgen-dependent disorders.

BACKGROUND OF THE INVENTION

An androgen-dependent condition, disease, disorder, or syndrome, is a medical condition that is, in part or full, dependent on, or is sensitive to, the presence of androgenic activity in the body. Known androgen-dependent conditions include acne, seborrhea, androgenic alopecia, telogen effluvium and hidradenitis suppurativa.

Hair loss, also known as alopecia or baldness, refers to a loss of hair from the head or body. Baldness can refer to general hair loss or male pattern hair loss. Male-pattern baldness or androgenetic alopecia accounts for more than 95% of hair thinning in adult men. Androgen-dependent disorders in general and specifically androgenetic alopecia have been correlated with increased levels of androgenic hormones in the roots of the hair follicle. Androgenic hormones reported to be over-produced in androgenic alopecia include dihydrotestosterone (DHT), a derivative of testosterone, or 5α-dihydrotestosterone (5α-DHT), also known as androstanolone (5α-androstan-17β-ol-3-one) as well as 17β-hydroxy-5α-androstan-3-one, a sex steroid and androgen hormone. The enzyme 5α-reductase synthesizes DHT in the prostate, testes, hair follicles, and adrenal glands. This enzyme reduces the 4,5 double-bond of the hormone testosterone. It is believed that the accumulation of androgenic hormones in the roots of the hair follicle leads to blockage of blood flow, reduced oxygen supply, and subsequent thinning of the hair.

*B. subtilis* is a gram-positive, rod-shaped bacterium found on skin, in the digestive tract, in epithelial wounds, on extremities of the human body including the human scalp. The strain is commercially used as a skincare product, a food ingredient for human consumption, in animal feed, in fertilizer, and in an antibiotic substitute. *B. subtilis* has several secretion systems, consisting of elements responsible of detection, transport and folding of secreted proteins. A common way to induce the secretion of a heterologous protein is via the addition of a naturally occurring signal peptide. Consequently, the widespread use of *B. subtilis* indicates its low-risk usability in commercial products, while its prevalence on the human scalp facilitates a pathway for microbiome engineering.

Inhibitors of 5α-reductase have been disclosed in U.S. Pat. Nos. 6,380,179 9,144,560 such as for alopecia. U.S. Pat. No. 6,710,037 discloses administration of 3α-HSD for the treatment of androgen-dependent disorders. An amino acid sequence of 3α-HSD and a *pseudomonas aeruginosa* 3α-HSD gene sequence, are disclosed in CN10090688 and CN2014/10591668, respectively.

There is an unmet need for novel therapies for treating androgen-dependent disorders, which are safe and have little or no side effects.

SUMMARY OF THE INVENTION

The present invention provides novel peptides, compositions and methods for treating androgen-dependent disorders, such as for inducing hair growth. In some embodiments, the present invention provides a chimeric polypeptide comprising a dihydrotestosterone (DHT) reductase fused to a signal peptide. In some embodiments, the invention provides an engineered microorganism expressing a polypeptide comprising a DHT reductase and a signal peptide.

According to one aspect, the present invention provides a chimeric polypeptide comprising a first moiety and a second moiety, the first moiety is a DHT reductase and the second moiety is a signal peptide.

According to some embodiments, the DHT reductase is 3 alpha HSD (3α-HSD) or a homolog thereof.

According to some embodiments, the 3α-HSD comprises the amino acid sequence as set forth in SEQ ID NO: 1 or an analog thereof having at least 85% sequence identity thereto.

According to some embodiments, the 3α-HSD comprises the amino acid sequence as set forth in SEQ ID NO: 3 or an analog thereof having at least 85% sequence identity thereto.

According to some embodiments, the signal peptide comprises the amino acid sequence as set forth in SEQ ID NO: 5 (MRSKKLWISLLFALTLIFTMAFSNMSVQA) or an analog thereof having at least 85% sequence identity thereto.

According to some embodiments, the signal peptide comprises an amino acid sequence selected from the group consisting of SEQ ID NOs: 5, 16-45 or an analog thereof having at least 85% sequence identity thereto. According to some embodiments, the signal peptide comprises the amino acid sequence selected from the group consisting of SEQ ID NOs: 5, 16, 17, 18, 19, 20, 21, 22, 23, 24, and 25 or an analog thereof having at least 85% sequence identity thereto. According to some embodiments, the signal peptide comprises the amino acid sequence selected from the group consisting of SEQ ID NOs: 17, 18, 19, and 20 or an analog thereof having at least 85% sequence identity thereto.

According to some embodiments, the signal peptide is attached to the DHT reductase via a peptide bond. According to some embodiments, the signal peptide is attached to the DHT reductase via a linker. According to some embodiments, the signal peptide is contiguous to the C-terminus or the N-terminus of the DHT reductase.

According to some embodiments, the chimeric polypeptide comprises the amino acid sequence as set forth in SEQ ID NO: 7.

According to another aspect, there is provided a polynucleotide molecule encoding the chimeric polypeptide of the invention. According to some embodiments, the polynucleotide molecule comprises the nucleotide sequence as set forth is SEQ ID NO: 8.

According to another aspect, there is provided an expression vector comprising the polynucleotide molecule of the invention.

According to another aspect, there is provided a composition comprising a first microorganism cell and a carrier, the first microorganism cell comprises a first polynucleotide molecule encoding a chimeric polypeptide of the present invention.

According to some embodiments, the first polynucleotide comprises the nucleotide sequence as set forth in SEQ ID NO: 8 and the second polynucleotide comprises the nucleotide sequence as set forth in SEQ ID NO: 9.

According to some embodiments, the first microorganism cell is capable of expressing and secreting the chimeric polypeptide.

According to some embodiments, the compositions of the invention further comprise any one of: (i) a DHT reductase cofactor; (ii) a second polynucleotide molecule encoding a DHT reductase cofactor producing enzyme, within the first microorganism cell; and (iii) a second microorganism cell, wherein the second microorganism cell comprises a second polynucleotide molecule encoding a DHT reductase cofactor producing enzyme.

According to some embodiments, the DHT reductase cofactor is selected from NADPH and NADH. According to some embodiments, the DHT reductase co-factor producing enzyme is Glucose-6-phosphate 1-dehydrogenase (Zwf). In some embodiments, Zwf comprises or consists of the amino acid sequence as set forth in SEQ ID NO: 9.

According to some embodiments, the first microorganism cell is a yeast or a fungus. According to some embodiments, the first microorganism cell is selected from the group consisting of: *Bacillus, Staphylococcus, Actinobacteria, Firmicutes, Proteobacteria, Bacteroidetes, Propionibacteria, Corynebacteria, Flavobacteria, lactobacillus, Escherichia coli, bifidobacteria, bacteroides,* and *Brevibacterium linens.*

According to some embodiments, the first microorganism cell is a *Bacillus* bacterium.

According to some embodiments, the second microorganism cell is an *Escherichia* bacterium.

According to another aspect, there is provided a kit comprising a first composition comprising a first microorganism cell, the first microorganism cell comprises a first polynucleotide sequence encoding a chimeric polypeptide of the present invention.

According to some embodiments, the kits of the invention further comprise a second composition, the second composition being selected from (i) a composition comprising a DHT reductase cofactor; and (ii) a composition comprising a second microorganism cell, the second microorganism cell comprises a second polynucleotide encoding a DHT reductase cofactor producing enzyme.

According to some embodiments, the kit is for treating an androgen-dependent disorder. According to some embodiments, the kit further comprises instruction for use of said kit for treatment or prevention of the androgen-dependent disorder. According to some embodiments, the kit further comprises an applicator for topically administering the first composition, and optionally the second composition, to a scalp of a subject in need thereof.

According to another aspect, there is provided a method for treating or ameliorating an androgen-dependent disorder in a subject in need thereof, the method comprising administering a first composition comprising a first microorganism cell, the first microorganism cell comprises a first polynucleotide molecule encoding a chimeric polypeptide of the invention, thereby treating or ameliorating an androgen-dependent disorder in the subject.

According to some embodiments, the method further comprises administering to the subject and a second composition, the second composition being selected from (i) a composition comprising a DHT reductase cofactor; and (ii) a composition comprising a second microorganism cell, the second microorganism cell comprises a second polynucleotide encoding a DHT reductase cofactor producing enzyme.

According to some embodiments, the androgen-dependent disorder is androgenic alopecia.

According to some embodiments, the administering is topically applying to the scalp of the subject.

According to another aspect, there is provided a method for determining (e.g., quantifying) the activity of a DHT reductase in a cell, the method comprising:
 i. providing a cell;
 ii. adding NADPH and dihydrotestosterone (DHT) to the cell; and
 iii. detecting the intensity of fluorescence of the lysate at 330-350 nm excitation and 440-470 nm emission;
 wherein a greater intensity of fluorescence is indicative of greater activity of the DHT reductase in the cell.

According to some embodiments, the intensity of fluorescence of the lysate is detected at about 340 nm excitation and 450 nm emission. According to some embodiments, the intensity of fluorescence of the lysate is detected at about 340 nm excitation and 460 nm emission. In some embodiments, the cell is a DHT reductase producing cell.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
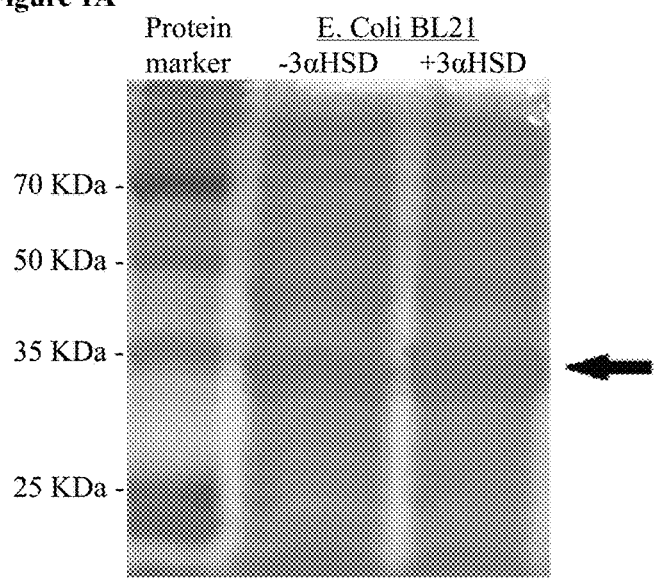
FIG. 1A: depicts SDS-PAGE analysis of over-expression of 3α-HSD enzyme (black arrow). Over-expression of the 3α-HSD enzyme was achieved by cloning of AKR1C9 gene under T7 promoter into pSB1C3 in *E. Coli* BL21 strain using restriction enzymes. The construct was confirmed by sequencing and SDS-PAGE.

The present invention provides novel compositions, methods and kits for treating, preventing or ameliorating androgen-dependent disorders, including but not limited to androgenic alopecia.

Chimeric Polypeptide

According to some embodiments, the present invention provides a chimeric polypeptide comprising a first moiety and a second moiety, the first moiety is a dihydrotestosterone (DHT) reductase and the second moiety is a signal peptide.

As used herein, a "dihydrotestosterone reductase", or "DHT reductase" is a protein capable of reducing a dihydrotestosterone molecule to an androstane molecule. Reduction reactions are well known to a person of skill in the art and involve a decrease in the oxidation state of a molecule, for example DHT. In some embodiments, the DHT reductase is 3 alpha-hydroxysteroid dehydrogenase (3α-HSD) or a homolog thereof. In some embodiments, the DHT reductase is 3 beta-hydroxysteroid dehydrogenase (3β-HSD) or a homolog thereof. In some embodiments, the DHT reductase is 17 beta-hydroxysteroid dehydrogenase (17β-HSD) or a homolog thereof.

In some embodiment, the 3α-HSD of the present invention reduces DHT to 5 alpha-androstane-3 alpha-17 beta-diol (3 alpha-diol). In some embodiments, the 3β-HSD of the present invention reduces DHT to androstane-3 beta-17 bet-diol (3 beta-diol). In some embodiments, the 17β-HSD of the present invention reduces DHT androstane-3,17-dione.

Examples of 3α-HSD include, but are not limited to, 3α-HSD type 1 enzyme, 3α-HSD type 2 enzyme and 3α-HSD type 3 enzyme. Examples of 3β-HSD, include but are not limited to, 3β-HSD type 1 enzyme, 3β-HSD type 2 enzyme. Examples of 17β-HSD, include but are not limited to, 17β-HSD type 2 enzyme, 17β-HSD type 4 enzyme and 17β-HSD type 6 enzyme.

In another embodiment, the 3α-HSD moiety is derived from or substantially corresponds to a 3α-HSD from an organism such as, but not limited to, a mammal, a vertebrate, a plant or a microorganism. In another embodiment, the 3α-HSD moiety is a human 3α-HSD. In some embodiments, a homolog of 3a HSD is mouse, rat, monkey, or any mammalian homolog of 3α-HSD.

In another embodiment, the 3β-HSD moiety is derived from or substantially corresponds to a 3β-HSD from an organism such as, but not limited to, a mammal, a vertebrate, a plant or a microorganism. In another embodiment, the 3β-HSD moiety is a human 3β-HSD. In some embodiments, a homolog of 3β-HSD is mouse, rat, monkey, or any mammalian homolog of 3β-HSD.

In another embodiment, the 17β-HSD moiety is derived from or substantially corresponds to a 17β-HSD from an organism such as, but not limited to, a mammal, a vertebrate, a plant or a microorganism. In another embodiment, the 17β-HSD moiety is a human 17β-HSD. In some embodiments, a homolog of 17β-HSD is mouse, rat, monkey, or any mammalian homolog of 17β-HSD.

In some embodiments, 3α-HSD is encoded by the AKR1C14 gene having the NCBI sequence ID: NM_138547.3 which encodes for a protein corresponding to NCBI accession number NP_612556.1. In some embodiments, the nucleotide sequence encoding 3α-HSD is set forth in SEQ ID NO: 4. AKR1C14 is also known as AKR1C9. In some embodiments, AKR1C14 encodes for a protein corresponding to NCBI accession number P23457. In some embodiments, the nucleotide sequence encoding 3α-HSD is set forth in SEQ ID NO: 2.

In another embodiment, the 3α-HSD moiety comprises the amino acid sequence as set forth in SEQ ID NO: 1 or an analog thereof having at least 85% sequence identity thereto. In some embodiments, the 3α-HSD moiety comprises the amino acid sequence as set forth in SEQ ID NO: 1 or an analog thereof having at least 70, 75, 80, 85, 90, 95, 97, or 99% sequence identity thereto. Each possibility represents a separate embodiment of the invention. In another embodiment, the 3α-HSD moiety consists of the amino acid sequence as set forth in SEQ ID NO: 1.

In another embodiment, the 3α-HSD moiety comprises the amino acid sequence as set forth in SEQ ID NO: 3 or an analog thereof having at least 85% sequence identity thereto. In some embodiments, the 3α-HSD moiety comprises the amino acid sequence as set forth in SEQ ID NO: 3 or an analog thereof having at least 70, 75, 80, 85, 90, 95, 97, or 99% sequence identity thereto. Each possibility represents a separate embodiment of the invention. In another embodiment, the 3α-HSD moiety consists of the amino acid sequence as set forth in SEQ ID NO: 3.

The term "signal peptide" (or interchangeably "secretion peptide") is defined herein as an amino acid sequence typically present at the N-terminal end of newly synthesized secretory or membrane polypeptides which directs the polypeptide across or into a cell membrane of the cell (e.g., the plasma membrane in prokaryotes). As such, a signal peptide includes peptides, polypeptides and proteins that, when fused to a protein moiety form a chimeric protein that is secreted more effectively by a host cell as compared to the secretion of the same protein moiety alone. In some embodiments, the signal peptide of the present invention is capable of directing a polypeptide (e.g., the chimeric polypeptide described herein) to a cell's secretory pathway. In some embodiments, the signal peptide of the present invention is capable of directing a polypeptide (e.g., the chimeric polypeptide described herein) into or across a cell membrane. In some embodiments, the signal peptide of the present invention is capable of directing a polypeptide (e.g., the chimeric polypeptide described herein) to the endoplasmic reticulum (ER), and into the membrane or the lumen of the ER.

Non-limiting examples of secretion peptides have been described by Antelmann H et. al, Genome Res. 2001 September; 11(9):1484-502, Wang G et. al., (Microb Cell Fact. 2015; 14(1):179), Bendtsen J D et. al., (BMC Microbiol. 2005 Oct. 7; 5:58) and Tjalsma H et. al., (Microbiol Mol Biol Rev. 2000 September; 64(3):515-47) and are selected from the group consisting of: Eno, PdhB, PdhD, YvgN, YwjH, CitH, RocA, RocF, Hagdual H, FlgKex, FliDex, KatAH, SodAH, YceD, Fus, Ef-G, GroEL, XepAex, XkdGex H, XkdKex, XkdMex, XlyAw ex, CwlCw ex, GapA, PdhA, albB, amyX, appB, estA, oppB, pbpX, phoD, qcrA, tlpA, wapA, wpra, adcB, yesM, yesW, yfkN, ykpC, ykuE, pghC, yubF, yuiC, tagV and efeB.

In some embodiments, a secretion peptide is used to increase the secretion of a protein moiety e.g., 3α-HSD. The signal peptide may be any polypeptide selected from a signal peptide known in the art as long as it is capable of secreting DHT reductase from a microorganism cell. Methods for determining whether a signal peptide is capable of secreting DHT reductase from a microorganism cell are known to one skilled in the art and are defined and exemplified herein. In some embodiments, the signal peptide of the invention are bacterial signal peptides. Non-limiting examples of bacterial signal peptides have the amino acid sequence as set forth in SEQ ID NO: 11 (MKLAACFLTLLPGFAVA), SEQ ID NO: 12 (MNDLNDFLKTILLSFIFFLLLSLPTVAEA), SEQ ID NO: 13 (MKKLAIMAAASMVFAVSSAHA), SEQ ID NO: 14 (MKLKFISMAVFSALTLGVATNAS), SEQ ID NO: 15 (MRTLQGWLLPVFMLPMAVYA), SEQ ID NO: 10 (MKKNTLLKVGLCVSLLGTTQFVSTISSVQA).

Other effective signal peptide coding regions for bacterial host cells may be obtained from the genes of *Bacillus* NCIB 11837 maltogenic amylase, *B. stearothermophilus* alpha-amylase, *B. licheniformis* subtilisin, *B. licheniformis* beta-lactamase, *B. stearothermophilus* neutral proteases (nprT, nprS, nprM) and *B. subtilis* prsS. Further signal peptides are described in Simonen and Palva (1993), Microbiological Reviews 57:109-137. Effective signal peptide coding regions for filamentous fungal host cells include but are not limited to the signal peptide coding regions obtained from *Aspergillus oryzae* TAKA amylase, *Aspergillus niger* neutral amylase, *Aspergillus niger* glucoamylase, *Rhizomucor miehei* asparatic proteinase, *Humicola insolens* cellulase and *Humicola lanuginosa* lipase. Variants of these signal peptides and other signal peptides are suitable, as well as expression mutants thereof having one or more silent mutations, as long as said signal peptide are effective in directing a polypeptide to and/or across the cell's membrane.

Additional, non-limiting examples of signal peptide are selected from the group of signal peptides that were described by UlfBrockmeier (dissertation, 2006), said group consisting of: Epr, YncM, YjfA, YfhK, Csn, LytD, Bpr, WapA, BglC, LytB, LipA, YckD, Pel, YnfF, PhrK, YbdN, YobB, Yddt, YhfM, BglS, Vpr, AprE, YjdB, YbbE, PhrC, GlpQ, SacC, YurI, PhoB, PenP, YfkD, YvpA, YdjM, AbnA, YwjE, YqgA, LipB, FliZ, DacB, SacB, YrvJ, YlaE, Pbp, YbxI, YolA, YqxI, YoaW, NprB, YlxF, YbfO, YlqB, SpoIID, YwmC, YvbX, YkvV, YlxY, XynA, SleB, YbbC, YxiT, LytC, PhrA, YkvT, CotC, AmyE, NprE, YolC, YqzG, YndA, YfjS, YvcE, YkwD, Mdr, YwfM, NucB, YqxM, YkoJ, Mpr, YpuA, TasA, YwmD, YwtD, YdbK, YfkN, YwaD, YpjP, RpmG, DacF, TyrA, LytF, WprA, YbbR, YhjA, YjiA, PbpD, YjcM, YhaK, PelB, SpoIIQ, MotB, YdhT, YbdG, LytE, PhrF, YhcR, CccA, CitH, AspB, YknX, YhdC, YlbL, YlxW, YngK, YnzA, YobV, YocH, YodV, YojL, YomL, YoqH, YoqM, YpbG, YpcP, YpmS, YpuD, YqzC, YraJ, YuaB, YusW, YvgO, YvgV, YvnB, YvpB, YwcI, YwdK, YweA, YwgB, YwmB, YwoF, YwqC, YwsB, YwtC, YwtF, YxaK, YxiA, YybN and YycP.

In some embodiments, the polynucleotide molecule encoding the signal peptide comprises the sequence GCAGCA or GCAGTA. In some embodiments, GCAGCA or GCAGTA is located between nucleotides 22-45 or 61-81 of the signal peptide provided herein. In some embodiments, the amino acid sequence of the signal peptide of the invention comprises the di-amino acid sequence alanine-alanine (AA), alanine-valine (AV) or alanine-leucine (AL). In some embodiments, AA, AV or AL is located between amino acids 8-15 or 21-27.

In one embodiment, the signal peptide is a polypeptide having an amino acid sequence which has at least 70%, at least 75%, at least 80%, at least 85%, at least 90%, at least 95%, at least 97% identity, or at least 99% identity to SEQ ID NO: 5. Each possibility represents a separate embodiment of the invention. In another embodiment, the signal peptide comprises or consists of an amino acid sequence as set forth in SEQ ID NO: 5.

In one embodiment, the signal peptide comprises the amino acid sequence selected from the group consisting of SEQ ID Nos: 16-45. In one embodiment, the signal peptide comprises the amino acid sequence selected from the group consisting of SEQ ID Nos: 16-25. In one embodiment, the signal peptide comprises the amino acid sequence selected from the group consisting of SEQ ID Nos: 17-20. In one embodiment, the signal peptide is a polypeptide having an amino acid sequence which has at least 70%, at least 75%, at least 80%, at least 85%, at least 90%, at least 95%, at least 97% identity, or at least 99% identity to the amino acid sequence selected from the group consisting of SEQ ID Nos: 16-45. Each possibility represents a separate embodiment of the invention. In one embodiment, the signal peptide is a polypeptide having an amino acid sequence which has at least 70%, at least 75%, at least 80%, at least 85%, at least 90%, at least 95%, at least 97% identity, or at least 99% identity to the amino acid sequence selected from the group consisting of SEQ ID Nos: 16-25. Each possibility represents a separate embodiment of the invention. In one embodiment, the signal peptide is a polypeptide having an amino acid sequence which has at least 70%, at least 75%, at least 80%, at least 85%, at least 90%, at least 95%, at least 97% identity, or at least 99% identity to the amino acid sequence selected from the group consisting of SEQ ID Nos: 17-20. Each possibility represents a separate embodiment of the invention. In one embodiment, the signal peptide is encoded by the nucleic acid sequence selected from SEQ ID Nos: 46-75. In one embodiment, the signal peptide is encoded by the nucleic acid sequence selected from SEQ ID Nos: 46-55. In one embodiment, the signal peptide is encoded by the nucleic acid sequence selected from SEQ ID Nos: 47-50.

In another embodiment, the DHT reductase moiety is attached to the signal peptide via a linker. In another embodiment, the DHT reductase moiety is attached to the signal peptide via a covalent bond. In another embodiment, the DHT reductase moiety is attached to the signal peptide via a peptide bond. In another embodiment, the DHT reductase moiety is attached to the signal peptide via a substituted peptide bond.

In another embodiment, the 3α-HSD moiety is attached to the signal peptide via a linker. In another embodiment, the 3α-HSD moiety is attached to the signal peptide via a covalent bond. In another embodiment, the 3α-HSD moiety is attached to the signal peptide via a peptide bond. In another embodiment, the 3α-HSD moiety is attached to the signal peptide via a substituted peptide bond.

In some embodiments, the signal peptide is fused to the N-terminus of a DHT reductase. In another embodiment, the signal peptide is fused to the C-terminus of a DHT reductase. In another embodiment, the signal peptide is operably linked to a DHT reductase. In some embodiments, the signal peptide is fused to the N-terminus of 3α-HSD. In another embodiment, the signal peptide is fused to the C-terminus of 3α-HSD. In another embodiment, the signal peptide is operably linked to 3α-HSD.

The term "operably linked" is intended to mean that the nucleotide sequence or amino acid sequence of interest is linked to the signal peptide (or nucleic acid sequence encoding the SP) in a manner that allows for expression and secretion of the nucleotide or amino acid sequence (e.g. in an in vitro transcription/translation system or in a host cell when the vector or polypeptide is introduced into the host cell).

In some embodiments, the chimeric polypeptide of the invention comprises the amino acid sequence:

(SEQ ID NO: 7)
MRSKKLWISLLFALTLIFTMAFSNMSVQAMDSISLRVALNDGNFIPVLGF

GTTVPEKVAKDEVIKAKIAIDNGFRHFDSAYLYEVEEEVGQAIRSKIEDG

TVKREDIFYTSKLWSTFHRPELVRTCLEKTLKSTQQDYVDLYIIHFPMAL

QPGDIFFPRDEHGKLLFETVDICDTWEAMEKCKDAGLAKSIGVSNFNCRQ

LERILNKPGLKYKPVCNQVECHLYLNQSKMLDYCKSKDIILVSYCTLGSS

RDKTWVDQKSPVLLDDPVLCAIAKKYKQTPALVALRYQLQRGVVPLIRSF

KPKRIKEPTQVFEFQLASEDMKALDGLNRNFRYNNAKYFDDHPNHPFTDE

The terms "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "moiety" refers to a part of a molecule that exhibits a particular set of chemical and pharmacological characteristics. A protein/polypeptide moiety refers to a protein/polypeptide or a fragment thereof that is capable of performing a defined biological activity.

The terms "chimeric polypeptide" as used herein refers to a non-natural protein or polypeptide comprising two or more protein/polypeptide moieties. In some embodiments, chimeric proteins are created through the joining of two or more genes that originally coded for separate proteins. Translation of this fusion gene results in a single or multiple polypeptides with functional properties derived from each of the original proteins. Recombinant fusion proteins may be created artificially by recombinant DNA technology for use in biological research or therapeutics. Chimeric or chimera usually designate hybrid proteins made of polypeptides having different functions or physico-chemical patterns.

The term "isolated" peptide refers to a peptide that is essentially free from contaminating cellular components, such as carbohydrate, lipid, or other proteinaceous impurities associated with the peptide in nature. Typically, a preparation of isolated peptide contains the peptide in a highly-purified form, i.e., at least about 80% pure, at least about 90% pure, at least about 95% pure, greater than 95% pure, or greater than 99% pure. Each possibility represents a separate embodiment of the invention.

One of skill in the art will recognize that individual substitutions, deletions or additions to a peptide, or protein sequence which alters, adds or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D). Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins, 1984).

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

The phrase "conservative substitution" also includes the use of a chemically derivatized residue in place of a non-derivatized residue provided that such peptide displays the requisite function of targeting mitochondria in a cell, as specified herein.

The term "derived from" or "corresponding to" refers to construction of a peptide based on the knowledge of a sequence using any one of the suitable means known to one skilled in the art, e.g. chemical synthesis in accordance with standard protocols in the art.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Those peptides, which contain one or more naturally occurring amino acid derivatives of the twenty standard amino acid residues are also included as chemical derivatives. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxylamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2-NH—, —CH2-S—, —CH2-S=0, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C-0-0-C (R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefmic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids. Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of performing the original biological activity.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptides of the invention may be synthesized or prepared by techniques well known in the art. The peptides can be synthesized by a solid phase peptide synthesis method of Merrifield (see J. Am. Chem. Soc, 85:2149, 1964). Alternatively, the peptides of the present invention can be synthesized using standard solution methods well known in the art (see, for example, Bodanszky, M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alphaamino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha, alpha)-dimethyl-3, 5 dimethoxybenzyloxycarbonyl, o-nitrophenylsulfenyl, 2-cyano-t-butyloxycarbonyl, 9-fluorenylmethyloxycarbonyl (FMOC) and the like.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

The peptides of the present invention, analogs or derivatives thereof produced by recombinant techniques can be purified so that the peptides will be substantially pure when administered to a subject. The term "substantially pure" refers to a compound, e.g., a peptide, which has been separated from components, which naturally accompany it. Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

Addition of amino acid residues may be performed at either terminus of the peptides of the invention for the purpose of providing a "linker" by which the peptides of this invention can be conveniently bound to a carrier. Such linkers are usually of at least one amino acid residue and can be of 40 or more residues, more often of 1 to 10 residues. Typical amino acid residues used for linking are tyrosine, cysteine, lysine, glutamic and aspartic acid, or the like.

Polynucleotides

In some embodiments, the invention provides a polynucleotide molecule encoding a chimeric polypeptide of the invention. In some embodiments, the polynucleotide molecule comprises the nucleotide sequence:

```
                                              (SEQ ID NO: 8)
atgcgttcaaaaaaactttggatctctcttcttttcgctcttacacttat cttcacaatggctttctcaaacatgtctgttcaagcgatggattccatat ctctgcgtgtagcactaaatgatggtaacttcattcctgtactggggttt ggaaccactgtgcctgagaaggttgctaaggatgaagttatcaaggctac taaaatagctatagataatggattccgccatttttgactctgcttatttgt acgaagtagaagaggaagtgggccaagccattagaagcaagattgaagac ggcactgtgaagagagaagatatattctatacttcaaagctttggagcac tttccatagaccagagctggtccgaacttgcttggaaaagacactgaaaa gcactcaacaggactatgtggatctttatattattcatttcccaatggca gcagcctggagatatattttcccacgagatgagcatggaaaactattgt ttgaaacagtggatatctgtgacacatgggaggccatggaaaagtgtaag gatgcaggattggccaagtctattggggtgtccaactttaactgtaggca gctggagaggattctgaataagccagggctcaaatacaagcctgtgtgca accaggtggaatgtcacctttatctcaaccagagcaaaatgctggactat tgtaagtcaaaagacatcattctggtttcctactgcacgctgggaagttc acgagacaaaacatgggtggatcagaaaagtccagttctcctagatgatc cagttctttgtgccatagcaaagaagtacaagcaaacccagccctagtt gcccttcgctaccagcttcagcgtggggttgtgccctgatcaggagttt caagccgaagcggatcaaagagccaacacaggtttttgaatttcagttg gcttcagaggacatgaaagccctggatggcttgaacagaaatttcagata caacaatgcaaaatattttgatgaccatcccaatcatccatttactgatg aatag.
```

The terms "polynucleotide" and "nucleic acid molecules" are used interchangeably herein and generally refer to a polymer of any length composed essentially of nucleotides, e.g., deoxyribonucleotides and/or ribonucleotides. Nucleic acids can comprise purine and/or pyrimidine bases, and/or other natural, chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted (such as, 2'-O-alkylated, e.g., 2'-O-methylated or 2'-O-ethylated; or 2'-O,4'-C-alkynelated, e.g., 2'-O,4'-C-ethylated) sugars or one or more modified or substituted phosphate groups. For example, backbone analogues in nucleic acids may include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs).

The term "polynucleotide" further specifically encompasses DNA, RNA and DNA/RNA hybrid molecules, specifically including hnRNA, pre-mRNA, mRNA, cDNA, genomic DNA, gene, amplification products, oligonucleotides, and synthetic (e.g. chemically synthesised) DNA, RNA or DNA/RNA hybrids. The terms "ribonucleic acid" and "RNA" as used herein mean a polymer of any length composed of ribonucleotides. The terms "deoxyribonucleic acid" and "DNA" as used herein mean a polymer of any length composed of deoxyribonucleotides. The term "DNA/RNA hybrid" as used herein mean a polymer of any length composed of one or more deoxyribonucleotides and one or more ribonucleotides.

A nucleic acid molecule can be naturally occurring, e.g., present in or isolated from nature, can be recombinant, i.e., produced by recombinant DNA technology, and/or can be, partly or entirely, chemically or biochemically synthesized. A nucleic acid molecule can be double-stranded, partly double stranded, or single-stranded. Where single-stranded, the nucleic acid can be the sense strand or the antisense strand. In addition, nucleic acid can be circular or linear.

The term "oligonucleotide" as used herein denotes single stranded nucleic acids (nucleotide multimers) of greater than 2 nucleotides in length and preferably up to 200 nucleotides in length, more preferably from about 10 to about 100 nucleotides in length, even more preferably from about 12 to about 50 nucleotides in length. Oligonucleotides can be synthesized by any method known in the art, e.g., by chemical or biochemical synthesis, e.g., solid phase phosphoramidite chemical synthesis, or by in vitro or in vivo expression from recombinant nucleic acid molecules, e.g., bacterial or retroviral vectors.

As used herein, a "recombinant nucleic acid" is a molecule where the nucleic acid molecule which encodes a polypeptide of interest has been modified in vitro, so that its sequence is not naturally occurring, or corresponds to naturally occurring sequences that are not positioned as they would be positioned in a genome which has not been modified.

Vectors, Promoters, and Expression Systems

In some embodiments, the invention provides an expression vector comprising a polynucleotide molecule of the invention.

The term "expression vector" refers herein to a DNA molecule, linear or circular, that comprises a segment encoding a polypeptide of the invention, and which is operably linked to additional segments that provide for its transcription.

As used herein, the term "expression" includes any step involved in the production of the polypeptide including, but not limited to, transcription, post-transcriptional modification, translation, post-translational modification, and secretion.

The present invention also relates to recombinant expression vectors comprising a polynucleotide of the present invention. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

Nucleic acid constructs of the present invention comprise a vector, such as, a plasmid, a cosmid, a phage, a virus, a bacterial artificial chromosome (BAC), a yeast artificial chromosome (YAC), and the like, into which a nucleic acid sequence of the invention has been inserted, in a forward or reverse orientation. In some embodiments, the construct further comprises regulatory sequences, including, for example, a promoter, operably linked to the sequence. Promoters are untranslated sequences located upstream (5') to the start codon of a structural gene (generally within about 100 to 1000 bp) that control the transcription and translation of a particular nucleic acid sequence, such as that encoding a chimeric protein as defined herein, to which they are operably linked. Large numbers of suitable vectors and promoters are known to those of skill in the art, and are commercially available.

Polynucleotides of the present invention can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

An expression vector optionally contains a ribosome binding site for translation initiation, and a transcription terminator, such as PinII. The vector also optionally includes appropriate sequences for amplifying expression, e.g., an enhancer.

The vector preferably contains one or more selectable markers that permit easy selection of transformed, transfected, transduced, or the like cells.

Examples of bacterial selectable markers are Bacillus licheniformis or Bacillus subtilis dal genes, or markers that confer antibiotic resistance such as ampicillin, chloramphenicol, kanamycin, neomycin, spectinomycin, or tetracycline resistance.

Introduction of a vector or DNA construct into a host cell can be effected by calcium phosphate transfection, DEAE-Dextran mediated transfection, electroporation, or other common techniques (See Davis, L., Dibner, M. and Battey, I. (1986) Basic Methods in Molecular Biology). The engineered host cells can be cultured in conventional nutrient media modified as appropriate for activating promoters, selecting transformants, or amplifying the polynucleotide of the present invention. Culture conditions, such as temperature, pH and the like, are those previously used with the host cell selected for expression, and will be apparent to those skilled in the art and in the references cited herein, including, for example, Sambrook, Ausubel and Berger, as well as, for example, Freshney (1994) Culture of Animal Cells, a Manual of Basic Technique, third edition, Wiley-Liss, New York; Payne et al. (1992) Plant Cell and Tissue Culture in Liquid Systems John Wiley and Sons, Inc. New York, N.Y.; Gamborg and Phillips (eds) (1995) Plant Cell, Tissue and Organ Culture; Fundamental Methods Springer Lab Manual, Springer-Verlag (Berlin Heidelberg New York) and Atlas and Parks (eds) The Handbook of Microbiological Media (1993) CRC Press, Boca Raton, Fla. In some embodiments, the vectors are introduced into host cells and/or microorganisms by standard methods including electroporation (e.g., as described in From et al., Proc. Natl. Acad. Sci. USA 82, 5824 (1985)), infection by viral vectors, high velocity ballistic penetration by small particles with the nucleic acid either within the matrix of small beads or particles, or on the surface (Klein et al., Nature 327. 70-73 (1987)), and/or the like.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Non-limiting examples of bacterial origins of replication are the origins of replication of plasmids pBR322, pUC19, pACYC177, and pACYC184 permitting replication in *E. coli*, and pUB110, pE194, pTA1060, and pAM beta 1 permitting replication in *Bacillus*.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The terms "regulatory sequences" and "control sequence" used herein are to be taken in a broad context and refer to regulatory nucleic acid sequences capable of driving and/or regulating expression of the sequences to which they are ligated (covalently linked) and/or operably, linked. The control sequences differ depending upon the intended host organism and upon the nature of the sequence to be expressed. For expression of a protein in prokaryotes, the control sequences generally include a promoter, a ribosomal binding site, and a terminator. In eukaryotes, control sequences generally include promoters, terminators and, in some instances, enhancers, and/or 5' and 3' untranslated sequences. The term 'control sequence' is intended to include, at a minimum, all components necessary for expression, and may also include additional advantageous components. According to some embodiments of the present invention, the control sequence is operable in a bacterium. The term "control sequence" encompasses a promoter or a sequence capable of activating or enhancing expression of a nucleic acid molecule in a host cell.

The term "operably linked" refers herein to a configuration in which a control sequence is appropriately placed at a position relative to the coding sequence of the DNA sequence such that the control sequence influences the expression of a polypeptide. When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

Promoters typically fall into two classes, inducible and constitutive. Inducible promoters are promoters that initiate increased levels of transcription from nucleic acid under their control in response to some change in culture conditions, e.g., the presence or absence of a nutrient or a change in temperature. At this time, a large number of promoters recognized by a variety of potential host cells are well known. These promoters are operably linked to nucleic acid encoding the polypeptide of interest by removing the promoter from the source nucleic acid by restriction enzyme digestion and inserting the isolated promoter sequence into the vector. Both the naturally occurring promoter sequence and many heterologous promoters may be used to direct amplification and/or expression of the polypeptide of interest. In general, plasmid vectors containing promoters and control sequences that are derived from species compatible with the host cell are used with these hosts. The vector ordinarily carries one or more replication sites as well as marker sequences, which are capable of providing phenotypic selection in transformed cells.

Promoters suitable for use with prokaryotic hosts include for example the beta-lactamase and lactose promoter systems, alkaline phosphatase, the tryptophan (trp) promoter system and hybrid promoters such as the tac promoter. However, other functional bacterial promoters are suitable. Their nucleotide sequences are generally known, thereby enabling a skilled worker operably to ligate them to nucleic acid encoding the protein secretion molecule as defined herein using linkers or adapters to supply any required restriction sites. Promoters for use in bacterial systems. A Shine-Dalgarno sequence may also be operably linked to the nucleic acid encoding the protein secretion molecule as defined herein.

According to some embodiments of the invention, the vectors comprise a constitutive promoter. Examples of constitutive promoters suitable for the constructs and methods according to the present invention include, but are not limited to, the CaMV35S promoter, GOS2, actin promoter, ubiquitin promoter, thiolase promoter.

According to another embodiment of the invention, the vectors comprise an inducible promoter. Examples of inducible promoters suitable for the constructs and methods according to the present invention include, but are not limited to, the lac promoter or xylose inducible promoter.

Other promoters known to control expression of genes in prokaryotic or eukaryotic cells or their viruses and which can be used in some embodiments of the invention include SV40 promoter, *E. coli* lac or trp promoter, phage lambda PL promoter, tac promoter, T7 promoter, and the like. Examples of suitable promoters useful for directing the transcription of the nucleotide constructs of the present invention in a filamentous fungal host cell are promoters such as cbh1, cbh2, egl1, egl2, pepA, hfb1, hfb2, xyn1, amy, and glaA (Nunberg et al., Mol. Cell Biol., 4:2306-2315 (1984), Boel et al., EMBO J. 3:1581-1585 ((1984) and EPA 137280). In bacterial host cells, suitable promoters include the promoters obtained from the *E. coli* lac operon, *Streptomyces coelicolor* agarase gene (dagA), a gene from a *Bacillus* sp., such as, for example, the *Bacillus subtilis* levansucranse gene (sacB), the *Bacillus licheniformis* alpha-amylase gene (amyl), the *Bacillus megaterium* InhA gene (which is described in U.S. Ser. No. 61/169,848, filed Apr. 16, 2009 and U.S. Ser. No. 12/760,827, filed Apr. 15, 2010), the *Bacillus stearothermophilus* maltogenic amylase gene (amyM), the *Bacillus amyloliquefaciens* alpha-amylase gene (amyQ), *Bacillus subtilis* xylA and xylB genes, the xylose promoter (Pxyl) from *Bacillus megaterium*, and the promoter obtained from the prokaryotic beta-lactamase gene.

Optionally, the present expression vectors will also contain sequences necessary for the termination of transcription and for stabilizing the mRNA, and may thus contain one or more transcription termination sequences. The term "transcription termination sequence" encompasses a control sequence at the end of a transcriptional unit, which signals 3' processing and termination of transcription. Additional regulatory elements, such as transcriptional or translational enhancers, may be incorporated in the expression construct.

The procedures used to ligate the elements described above to construct the recombinant expression vectors of the present invention are well known to one skilled in the art.

Secreting Microorganisms

In another embodiment, the present invention provides a composition comprising a cell of at least one microorganism (also termed herein "a first microorganism"), e.g., bacteria, and a carrier, said microorganism comprising a first polynucleotide molecule encoding a chimeric polypeptide of the invention. In some embodiment, the microorganism cell comprises a polynucleotide sequence encoding a DHT reductase and a signal peptide. In some embodiment, the microorganism cell comprises a polynucleotide sequence encoding 3α-HSD and a signal peptide. In some embodiments, the microorganism is capable of expressing and secreting the chimeric polypeptide.

In another embodiment, the composition of the invention further comprises a cofactor to a DHT reductase. In another embodiment, the composition of the invention further comprises a cofactor to 3α-HSD. The term "cofactor" as used herein refers to a non-protein chemical compound that is required for a protein's (e.g., an enzyme's) activity. In some embodiments, the cofactor to the DHT reductase is NADPH. In some embodiments, the cofactor to the DHT reductase is NADH. In some embodiments, the cofactor to 3α-HSD is NADPH. In some embodiments, the cofactor to 3α-HSD is NADH.

In some embodiments, the microorganism comprises a second polynucleotide encoding a cofactor producing enzyme. In some embodiments, the microorganism comprises a second polynucleotide encoding a DHT reductase cofactor producing enzyme. In some embodiments, enzyme is a 3α-HSD cofactor producing enzyme. In some embodiments, the microorganism is capable of producing/expressing the cofactor producing enzyme. In some embodiments, the cofactor producing enzyme is capable of producing the cofactor within the cell.

In another embodiment, the present invention provides a composition comprising at least one engineered microorganism (e.g., bacterial cell) comprising a first polynucleotide sequence encoding a DHT reductase fused to a signal peptide and a second polynucleotide sequence encoding an enzyme capable of producing a DHT reductase cofactor (e.g., NADPH). In another embodiment, the present invention provides a composition comprising at least one engineered microorganism (e.g., bacterial cell) comprising a first polynucleotide sequence encoding 3α-HSD fused to a signal peptide and a second polynucleotide sequence encoding an enzyme capable of producing a 3α-HSD cofactor (e.g., NADPH).

In some embodiments, the enzyme is glucose-6-phosphate 1-dehydrogenase (Zwf). Zwf is known in the art as an enzyme that catalyzes the conversation of D-glucose 6-phosphate to 6-phospho-D-glucono-1,5-lactone while generating NADPH from NADP+. In some embodiments, Zwf has the amino acid sequence as set forth in SEQ ID NO:9.

In another embodiment, the present invention provides a composition comprising at least two microorganisms (e.g., bacterial cells), wherein a first microorganism cell comprises a first polynucleotide sequence encoding a DHT reductase fused to a signal peptide and a second microorganism cell comprises a second polynucleotide sequence encoding an enzyme capable of producing a DHT reductase co-factor (e.g., NADPH). In another embodiment, the present invention provides a composition comprising at least two microorganisms (e.g., bacterial cells), wherein a first microorganism cell comprises a first polynucleotide sequence encoding 3α-HSD fused to a signal peptide and a second microorganism cell comprises a second polynucleotide sequence encoding an enzyme capable of producing a 3α-HSD co-factor (e.g., NADPH).

In another embodiment, the present invention provides a composition comprising at least two microorganisms (e.g., bacterial cells), wherein a first microorganism cell comprises a first polynucleotide comprising the nucleotide sequence as set forth in SEQ ID NO: 8 and a second microorganism cell comprises a second polynucleotide sequence encoding an enzyme capable of producing a 3α-HSD co-factor (e.g., NADPH). In some embodiments, the enzyme is glucose-6-phosphate 1-dehydrogenase (Zwf). In some embodiments, the second polynucleotide sequence comprises the sequence set forth in SEQ ID NO: 9.

The term "expressing" as used herein refers to the biosynthesis of a polynucleotide-encoded product, including the transcription and/or translation of the product. Thus, expression of a polynucleotide sequence may refer to transcription of the polynucleotide sequence (e.g., transcription resulting in mRNA or other functional RNA) and/or translation of RNA into a precursor or mature protein (polypeptide).

In some embodiments, the polynucleotide sequence encoding a DHT reductase fused to a signal peptide is introduced to the microorganism (e.g., bacterium) using an expression vector. In some embodiments, the polynucleotide sequence encoding 3α-HSD fused to a signal peptide is introduced to the microorganism (e.g., bacterium) using an expression vector.

In another embodiment, the polynucleotide sequence encoding a DHT reductase fused to a signal peptide is introduced to the genome of the microorganism (e.g., bacterium). In another embodiment, the polynucleotide sequence encoding 3α-HSD fused to a signal peptide is introduced to the genome of the microorganism (e.g., bacterium).

In some embodiments, the microorganism of the invention is an engineered microorganism. The term "engineered microorganism" as used herein refers to any cell to which a polynucleotide of the present invention is introduced, wherein said cell is capable of expressing the polypeptide encoded by said polynucleotide. An engineered microorganism of the present invention can be selected from bacteria, yeast, fungus or any of a variety of other microorganisms applicable to recombinant protein expression and secretion processes. In some embodiments, the engineered microorganism is adapted to target (e.g., home) on a target site for a pre-determined period of time. In some embodiments, the target site is a scalp of a subject. Non-limiting examples of bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*. Non-limiting examples of yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*.

In another embodiment, the bacterial cell of the present invention belongs to a strain that exhibits minimal or no pathogeny to humans. By minimal or no pathogeny, it is meant that the bacterial strain does not cause illnesses in humans. Non-limiting examples of minimal or non-pathogenic bacteria are selected from the list comprising: *staphylococcus* (*S. epidermis, S. aureus*), *lactobacillus* (*L. plantarum, L. reuteri* and *L. acidophilus*), *Escherichia coli, bifidobacteria, bacteroides* and *Brevibacterium linens*.

In another embodiment, the microorganism of the present invention belongs to a strain of the skin flora. The term "skin flora" or "skin microbiota" refers to microorganisms which reside on the skin. There are more than a 1000 bacterial species that belong to the skin flora, most of which are found in the superficial layers of the epidermis and the upper parts of hair follicles. Skin flora is usually non-pathogenic, and either commensal (are not harmful to their host) or mutualistic (offer a benefit). Non-limiting examples of skin flora are selected from the list comprising: *Bacillus* (*B. subtilis*), *Staphylococcus* (i.e., *S. epidermidis* and *S. aureus*), Actinobacteria, Firmicutes, Proteobacteria, Bacteroidetes, Propionibacteria, Corynebacteria and Flavobacteria.

In some embodiments, the bacterial cell of the present invention is from the genus *Escherichia*. As used herein, the term "*Escherichia*" includes all species within the genus *Escherichia*, as known to those of skill in the art, including but not limited to, *E. coli, E. adecarboxylata, E. albertii, E. blattae, E. fergusonii, E. hermannii, E. senegalensis*, and *E. vulneris*. The genus "*Escherichia*" is defined as Gram-negative, non-spore forming, facultatively anaerobic, rod-shaped bacteria that are classified as members of the Family Enterobacteriaceae, Order Enterobacteriales, Class Gamma Proteobacteria.

In some embodiments, the bacterial cell of the present invention is from the genus *Bacillus*. As used herein, the term "*Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to, such organisms as *B. stearothermophilus*, which is now named "*Geobacillus stearothermophilus*". The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

In some embodiments, the present application is directed to a method for the production and secretion by a host cell (e.g., a bacterial host cell), of at least one polypeptide of interest in a biologically active form comprising introducing into said host cell a polynucleotide molecule or a vector according to the invention under conditions effective to cause expression of the encoded chimeric polypeptide of the invention, wherein the encoded chimeric polypeptide is secreted by the host cell into the environment of said host cell.

During secretion, a signal peptide may be cleaved from said chimeric polypeptide such that the chimeric polypeptide is released in the host environment (e.g. a culture medium). In some embodiments, a protease target sequence introduced in the linker connecting the carrier domain to the functional domain and the protein of interest is cleaved by protease(s) to release in the host environment the protein of interest cleaved from the remaining chimeric polypeptide.

The environment of said host cell is intended to refer to the place wherein said bacterium is grown. In another embodiment, the environment of said bacterium may be a tissue of a living being, e.g. a human or animal tissue, in particular in the case of therapeutic applications contemplated in the present invention.

The invention further relates to the use of a signal peptide for controlling the secretion of a polypeptide of interest, preferably a polypeptide as defined herein. In this context, it shall be noted that the term "controlling the secretion" is intended to encompass generation, induction, and/or the improvement of secretion. More particularly, the invention is directed to the use of a signal peptide as defined herein, for controlling the secretion of a polypeptide of interest, preferably a polypeptide as defined herein, by a host cell.

With "improvement of secretion" is meant that the amount of polypeptide of interest secreted is higher, such as at least 1.5, 3, 2.5, 5 or 10 percent higher, than the amount obtained in the case no signal peptide is used to control the secretion.

Pharmaceutical Compositions

In some embodiments, there is provided a pharmaceutical composition comprising as an active ingredient a therapeutically effective amount of microbial host cells of the present invention, and a pharmaceutically acceptable carrier or diluents.

In some embodiments, the composition of the invention comprises medium suitable for growth of the microorganism of the present invention. As used herein, the term "growth medium" refers to a solution used to culture microorganisms. Any growth medium suitable for culturing microorganism cells can be used. For commercial production, the growth medium will naturally be optimized in terms of the yield. Non-limiting examples of suitable growth media are commercially available growth media, such as M9 and LB (available from several manufacturers, such as Fermentas, Lithuania). In some embodiments, the pharmaceutical composition further comprises microorganism growth medium supplemented with 50%, 60%, 70%, 80% or 90% glycerol. Each possibility represents a separate embodiment of the invention.

In some embodiments, microorganisms are subjected to lysis and the resulting lysate is formulated into a composition. The formulation may comprise the step of treating the lysate so as to remove or inactivate intact bacteria in the lysate, for example, by partitioning intact bacteria from the lysate. The lysate may be subject to purification of filtration steps to remove other components, such as bacterial growth media or contaminants.

In some embodiments, intact bacteria are formulated as a composition. The bacteria may be inactivated prior to, or after, formulation into a composition. The bacteria may be subject to a purification or filtration step so as to remove other components, such as bacterial growth media or contaminants.

The compositions prepared by such a method may be suitable for use in treatment, for example in treating androgen disorders. Such methods may involve the addition of one or more pharmaceutically or cosmetically acceptable carrier and/or excipients.

The compositions according to the invention may be in any of the formulating forms that are normally available for the method of administration selected.

The carrier (e.g., vehicle) may be of diverse nature depending on the type of composition under consideration. The compositions for topical administration may be aqueous, aqueous-alcoholic or oily solutions, dispersions of the solution type or dispersions of the lotion or serum type, emulsions of liquid or semi-liquid consistency, of the milk type, suspensions or emulsions of the cream type, aqueous or anhydrous gels, microemulsions, microcapsules, microparticles, or vesicular dispersions of ionic and/or non-ionic type. These compositions are prepared according to the usual methods.

As used herein, the term "carrier," or "excipient" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some nonlimiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

In a known manner, the formulations for topical administration may also contain adjuvants that are customary in the cosmetics, pharmaceutical and/or dermatological field, such as hydrophilic or lipophilic gelling agents, hydrophilic or lipophilic active agents, preservatives, antioxidants, solvents, fragrances, fillers, screens, bactericides, odor absorbers and colorants. The amounts of these various adjuvants are those conventionally used in the field under consideration, and are, for example, from 0.01% to 20% of the total weight of the composition. Depending on their nature, these adjuvants may be introduced into the fatty phase and/or into the aqueous phase.

A formulation may contain a single (unit) dose of microorganism, or lysate thereof. Suitable doses of microorganism (intact or lysed) may be in the range $10^4$ to $10^{12}$ colony forming units (cfu), e.g. one of $10^4$ to $10^{10}$, $10^4$ to $10^8$, $10^6$ to $10^{12}$, $10^6$ to $10^{10}$, or $10^6$ to $10^8$ cfu.

In some embodiments, doses may be administered once or twice daily. In some embodiments, a formulation for use according to the present invention may comprise at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 120.0%, about 13.0%, about 14.0%, about 15.0%, about 16.0%, about 17.0%, about 18.0%, about 190.0%, about 20.0%, about 25.0%, about 30.0%, about 35.0%, about 40.0%, about 45.0%, about 50.0% by weight of microorganism or lysate thereof. Each possibility represents a separate embodiment of the invention.

In some embodiments, the formulation may comprise, one of at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5%, by weight of microorganism or lysate thereof. Each possibility represents a separate embodiment of the invention.

In some embodiments, the pharmaceutical composition comprises one microorganism strain.

In some embodiments, the pharmaceutical composition comprises at least two microorganism strains. In some embodiments, a first microorganism is *Escherichia* and a second microorganism is *Bacillus*. In some embodiments, a first microorganism is *Bacillus* and a second microorganism is *Escherichia*.

In some embodiments, the first microorganism and the second microorganism are of the same species. In some embodiments, the first microorganism and the second microorganism are *Bacillus*. In some embodiments, the first microorganism and the second microorganism are *Escherichia*.

In some embodiments, the pharmaceutical composition comprises a first microorganisms and a second microorganism, wherein the ratio of the number of microorganism cells of the first microorganism to the second microorganism is selected from: 1:1-1:2, 1:1-1:3, 1:1-1:4, 1:1-1:5, 1:1-1:10, 1:1-1:20, 1:1-1:30, 1:1-1:40, 1:1-1:50, 1:1-1:100, 1:1-1:200, 1:1-1:300, 1:1-1:400, 1:1-1:500, 1:1-1:103, 1:1-1:104 or 1:1-1:105. Each possibility represents a separate embodiment of the invention.

In some embodiments, the pharmaceutical composition comprises a first microorganisms and a second microorganism, wherein the ratio of the number of microorganism cells of the second microorganism to the first microorganism is between 1:1 to 1:2, 1:1 to 1:5, 1:5 to 1:10, 1:10 to 1:50, 1:10 to 1:100, 1:100 to 1:500, 1:1 to 1:500, 1:1 to 1:103, 1:1 to 1:104 or 1:1 to 1:105. Each possibility represents a separate embodiment of the invention.

Androgen-Dependent Disorders

In another embodiment, the present invention provides a kit for treating, delaying the onset, delaying progression of, reducing the incidence of or reducing the severity of an androgen-dependent disorder in a subject, the kit comprising a first composition comprising a first microorganism cell, the first microorganism cell comprises a first polynucleotide sequence encoding a chimeric polypeptide of the invention; and optionally a second composition comprising any one of: (i) a DHT reductase cofactor; or (ii) a second microorganism cell, the second microorganism cell comprises a second polynucleotide encoding a DHT reductase cofactor producing enzyme.

In another embodiment, the present invention provides a method of treating, delaying the onset, delaying progression of, reducing the incidence of or reducing the severity of an androgen-dependent disorder in a subject, the method comprising administering to a subject a chimeric polypeptide of the invention, an expression vector of the invention, a pharmaceutical composition of the present invention, or the first and second compositions of a kit of the invention, thereby treating a subject afflicted with an androgen-dependent disorder.

An androgen-dependent disorder refers to any disorder that depends on androgen stimulation. In one embodiment, said androgen-dependent disorder is a disorder that benefits from a decrease in androgen stimulation. An androgen-dependent disorder can result from an excessive accumulation of testosterone or other androgenic hormone; increased sensitivity of androgen receptors to androgen; or an increase in androgen-stimulated transcription. Non-limiting examples of androgen-dependent disorders include acne, seborrhea, androgenic alopecia, telogen effluvium and hidradenitis suppurativa. In some embodiments, the androgen-dependent disorder is androgenic alopecia.

In some embodiments, the term "treatment" as used herein refers to any response to, or anticipation of androgen-dependent disorder and includes but is not limited to: preventing the androgen-dependent disorder from occurring in a subject, which may or may not be predisposed to the condition, but has not yet been diagnosed with an androgen-dependent disorder and accordingly, the treatment constitutes prophylactic treatment for androgen-dependent disorders; inhibiting androgen-dependent disorder, e.g., arresting, slowing or delaying the onset, development or progression of the androgen-dependent disorder; or relieving androgen-dependent disorder, e.g., causing regression of the androgen-dependent disorder or reducing the symptoms of androgen-dependent disorder.

In some embodiments, the treatment of the present invention results in alleviation of at least one symptom of an androgen-dependent disorder of the treated subject.

In some embodiments, the treatment of the present invention results in prevention, slowing or delaying the onset, development or progression of hair loss of the treated subject.

In some embodiments, the treatment of the present invention results in induction of hair growth of the treated subject.

In some embodiments, the treatment of the present invention results in increase in average hair width of the treated subject.

In some embodiments, the treatment of the present invention results in alleviation of acne symptoms of the treated subject.

In some embodiments, the treatment of the present invention results in alleviation of seborrhea related symptoms, such as but not limited to dermatitis of the treated subject.

In another embodiment, the term "administering" as used herein, includes delivery of effective amounts of the composition of the present invention to a subject in need thereof. In some embodiments, administering is topical administration. In some embodiments, administering comprises administering to the skin. In some embodiments, administering comprises administration to the scalp. In some embodiments, administering is topically applying to the scalp of the subject.

In some embodiments, the pharmaceutical composition comprises microorganism cells of the present invention and dosages may range from $1\times10^6$ to $1\times10^7$ microorganism cells per day, from $1\times10^7$ to $1\times10^8$ microorganism 1 cells per day, from $1\times10^8$ to $1\times10^9$ microorganism cells per day, from $1\times10^9$ to $1\times10^{10}$ microorganism cells per day, from $1\times10^{10}$ to $1\times10^{11}$ microorganism cells per day. Each possibility represents a separate embodiment of the invention. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

In some embodiments, the pharmaceutical composition of the present invention is delivered to a surface of the body of a subject, e.g., skin and more specifically the scalp. The delivery of a pharmaceutical composition comprising microorganisms to a surface of the subject may be done by any method suitable for dispensing liquid on a surface. Non-limiting examples for means to dispense the pharmaceutical composition onto a surface of the body of a subject are selected from the list comprising: a syringe, a spray container, a fabric, a cloth, a brush or a sponge.

In order to treat a patient, a therapeutically effective dose of the pharmaceutical composition of the present invention is administered. By "therapeutically effective dose" herein is meant a dose that produces the effects for which it is administered. The exact dose will depend on the purpose of the treatment, and will be ascertainable by one skilled in the art using known techniques.

The treatment method of the invention may be carried out in particular by orally and/or topically administering at least an effective amount of at least one microorganism in accordance with the invention.

Topical administration comprises the external application, to the skin, of cosmetic and/or dermatological compositions according to the customary technique for using these compositions.

By way of illustration, the treatment method according to the invention may be carried out by topical application, for example daily, of the microorganism in accordance with the invention, which may, for example, be formulated in the form of creams, gels, sera, lotions, emulsions, makeup-removing milks or after-sun compositions.

The method according to the invention may comprise a single application. According to another embodiment, the application is repeated, for example, 2 to 3 times a day, for one day or more, and generally for a sustained period of at least 4, or even 1 to 15, weeks.

Methods for Determining the Activity of 3α-HSD

In some embodiments, there is provided a method for determining the activity of a DHT reductase in a biological sample. In some embodiments, there is provided a method for determining the activity of 3α-HSD in a biological sample. The method is based on quantification of the cofactor NADPH is the sample. NADPH concentration can be quantified using fluorescence due to its excitation and emission curves which peak at 340 nm and at 460 nm respectively. In some embodiments, there is provided a method for determining the activity of a DHT reductase in a cell. In some embodiments, there is provided a method for determining the activity of 3α-HSD in a cell. The method is based on quantification of the co-factor NADPH is the cell. NADPH concentration can be quantified using fluorescence due to its excitation and emission curves which peak at 340 nm and at 450 nm respectively.

The term "biological sample" as used herein refers to any sample that comprises a living organism or parts of a living organism e.g., tissue. Non-limiting examples of biological samples of the present invention include, but are not limited to, a bacterial cell suspension, a bacterial lysate, bacterial growth medium, blood, saliva and urine.

In some embodiments, there is provided a method for determining the activity of a DHT reductase in a biological sample, the method comprising:
 i. providing a biological sample;
 ii. adding NADPH and DHT to the cell;
 iii. quantifying final NADPH concentration;
wherein the NADPH concentration is indicative of the activity of the DHT reductase in the biological sample.

In some embodiments, there is provided a method for determining the activity of a DHT reductase in a cell, the method comprising:
 iv. providing a cell;
 v. adding NADPH and DHT to the cell;
 vi. quantifying final NADPH concentration;
wherein the NADPH concentration is indicative of the activity of the DHT reductase in the cell.

In some embodiments, the DHT reductase is 3α-HSD. In some embodiments, the cell is a DHT reductase producing cell. In some embodiments, the cell is a 3α-HSD producing cell.

In some embodiments, the concentration of DHT is between 0.1 μM to about 1 μM, between 1 μM to about 10 μM, between 10 μM to about 100 μM, between 60 μM to about 100 μM, between 60 μM to about 300 μM, between 60 μM to about 500 μM, between 60 μM to about 1 mM. Each possibility represents a separate embodiment of the invention.

In some embodiments, the concentration of NADPH is between 0.1 μM to about 1 μM, between 1 μM to about 10 μM, between 10 μM to about 100 μM, between 60 μM to about 100 μM, between 60 μM to about 300 μM, between 60 μM to about 500 μM, between 60 μM to about 1 mM. Each possibility represents a separate embodiment of the invention.

In some embodiments, there is provided a method for determining the activity of a DHT reductase in a biological sample, the method comprising:
 i. providing a biological sample;
 ii. adding NADPH and DHT to the biological sample;
 iii. detecting the intensity of fluorescence of said lysate at 330-350 nm excitation and 440-470 nm emission;
wherein the intensity of fluorescence is indicative of the activity of the DHT reductase in the biological sample. In some embodiments, a greater intensity of fluorescence is indicative of greater activity of the DHT reductase in the biological sample.

In some embodiments, there is provided a method for determining the activity of a DHT reductase in a cell, the method comprising:
 i. providing a cell;
 ii. adding NADPH and DHT to the cell;
 iii. detecting the intensity of fluorescence of said lysate at 330-350 nm excitation and 440-470 nm emission;
wherein a greater intensity of fluorescence is indicative of greater activity of the DHT reductase in the cell. In some embodiments, the intensity of fluorescence is indicative of the activity of the DHT reductase in the cell. In some embodiments, the DHT reductase is 3α-HSD.

In some embodiments, the intensity of fluorescence is detected at about 340 nm excitation and about 450 nm emission. In some embodiments, the intensity of fluorescence of said biological sample is detected at about 340 nm excitation and about 460 nm emission. In some embodiments, the intensity of fluorescence is detected at 340 nm excitation and 450 nm emission. In some embodiments, the intensity of fluorescence of said biological sample is detected at 340 nm excitation and 460 nm emission.

In some embodiment, quantifying final NADPH concentration is detecting the intensity of fluorescence at about 340 nm excitation and 460 nm emission. In some embodiment, the quantifying final NADPH concentration is detecting the intensity of fluorescence at about 340 nm excitation and about 450 nm emission. In some embodiment, quantifying final NADPH concentration is detecting the intensity of fluorescence at 330-350 nm excitation and 440-470 nm emission.

In some embodiments, the intensity of fluorescence is detected in the cell. In some embodiments, the intensity of fluorescence is detected in the biological sample. In some embodiments, the intensity of fluorescence is detected in a lysate of the cell or biological sample.

In some embodiments, incubation time is between 1-5 min, 1-10 min, 5-10 min, 10-20 min, 10-30 min, 10-60 min, 30-60 min, 30-90 min or 30-120 min. Each possibility represents a separate embodiment of the invention.

In some embodiments, incubation temperature is about 37° C. In some embodiments, the incubation temperature is between 30° C.–37° C. In some embodiments, the incubation temperature is between 35° C.–38° C. In some embodiments, the incubation temperature is between 30° C.–37° C.

In some embodiments, there is provided a kit for determining the activity of 3α-HSD in a cell, the kit comprising: cell lysis reagent; NADPH; and DHT.

In some embodiments, there is provided a kit for determining the activity of 3α-HSD in a biological sample, the kit comprising: NADPH; and DHT.

In some embodiments, the kit further comprises a reaction buffer.

In some embodiments, the kit further comprises instructions for use.

In some embodiments, the kit further comprises a labeling moiety, wherein said labeling moiety can bind NADPH, and wherein the binding of said labeling moiety to NADPH produces a detectable signal.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Solutions:

DHT solution: 2.9044 milligrams of DHT (analytical weight) were added into a 1.5 ml tube. Next, 1 ml of the Methanol were added and the solution was sterilized by filtration to a new 1.5 ml tube. NADPH Solution: A standardized 0.1 M NaOH solution was diluted by a factor of 10 (0.01M NaOH solution). Next, 1 ml of 0.1M solution was added to 9 ml sterilized water. A weight of 4.1668 milligrams of NADPH*Na4 (analytical weight) was added into a 1.5 ml tube. Next, 0.5 ml of the diluted solution were transferred to a new 1.5 ml tube covered in aluminum foil, on ice and in dimmed lighting. The tube was vortexed and its content was sterilized by filtration to a new 1.5 ml tube.

DNA Sequences and Parts for Examples 1-3:

Silent mutations in the AKR1C9 isoform were performed in nucleotide base pairs at three restriction sites: EcoRI and two PstI. The DNA fragment was synthesized using standard methods.

The amino acid sequence of the signal peptide is set forth in SEQ ID NO: 5. In some embodiments, the nucleotide sequence encoding for the signal peptide was optimized for B. subtilis by codon optimization and has the nucleotide sequence as set forth in SEQ ID NO: 6. The signal peptide was synthesized by standard methods and cloned on pDR111 backbone by PCR. Further sequences employed in the following examples are presented in Table 1.

TABLE 1

| SEQ ID NO: | Description | Sequence |
|---|---|---|
| 1 | 3α-HSD (AKR1C9) amino acid sequence | MDSISLRVALNDGNFIPVLGFGTTVPEKVAKDEVIKATKIAID NGFRHFDSAYLYEVEEEVGQAIRSKIEDGTVKREDIFYTSKL WSTFHRPELVRTCLEKTLKSTQQDYVDLYIIHFPMALQPGDIF FPRDEHGKLLFETVDICDTWEAMEKCKDAGLAKSIGVSNFNC RQLERILNKPGLKYKPVCNQVECHLYLNQSKMLDYCKSKDII LVSYCTLGSSRDKTWVDQKSPVLLDDPVLCAIAKKYKQTPA LVALRYQLQRGVVPLIRSFKPKRIKEPTQVFEFQLASEDMKAL DGLNRNFRYNNAKYFDDHPNHPFTDE |
| 2 | AKR1C9 (3α-HSD) | atggattccatatctctgcgtgtagcactaaatgatggtaacttcattcctgtactggggtttggaac cactgtgcctgagaaggttgctaaggatgaagttatcaaggctactaaaatagctatagataatg gattccgccattttgactctgcttatttgtacgaagtagaagaggaagtgggccaagccattagaa gcaagattgaagacggcactgtgaagagagaagatatattctatacttcaaagctttggagcact tccatagaccagagctggtccgaacttgcttggaaaagacactgaaaagcactcaacaggact atgtggatctttatattattcatttcccaatggctttgcagcctggagatatattttccccacgagatg agcatggaaaactattgtttgaaacagtggatatctgtgacacatggaggccatggaaaagtgt aaggatgcaggattggccaagtctattggggtgtccaactttaactgtaggcagctggagagga ttctgaataagccagggctcaaatacaagcctgtgtgcaaccaggtggaatgtcacctttatctca accagagcaaaatgctggactattgtaagtcaaaagacatcattctggtttcctactgcacgctgg gaagttcacgagacaaaacatgggtggatcagaaaagtccagttctcctagatgatccagttctt tgtgccatagcaaagaagtacaagcaaaccccagccctagttgccatcgctaccagatcagc gtggggttgtgccctgatcaggagtttcaagccgaagcggatcaaagagccaacacaggtttt tgaatttcagttggcttcagaggacatgaaagccctggatgccttgaacagaaatttcagataca acaatgcaaatattttgatgaccatcccaatcatccatttactgatgaatag |
| 3 | AKR1C14 (3α-HSD) Amino Acid sequence | MDSISLRVALNDGNFIPVLGFGTTVPEKVAKDEVIKATKIAI DNGFRHFDSAYLYEVEEEVGQAIRSKIEDGTVKREDIFYTSK LWSTFHRPELVRTCLEKTLKSTQLDYVDLYIIHFPMALQPGD IFFPRDEHGKLLFETVDICDTWEAMEKCKDAGLAKSIGVSNF NCRQLERILNKPGLKYKPVCNQVECHLYLNQSKMLDYCKS KDIILVSYCTLGSSRDKTWVDQKSPVLLDDPVLCAIAKKYK QTPALVALRYQLQRGVVPLIRSFNAKRIKELTQVFEFQLASE DMKALDGLNRNFRYNNAKYFDDHPNHPFTDE |
| 4 | AKR1C14 (3α-HSD) | atggattccatatctctgcgtgtagcactaaatgatggtaacttcattcctgtactggggtttggaacc actgtgcctgagaaggttgctaaggatgaagttatcaaggctactaaaatagctatagataatggat tccgccattttgactctgcttatttgtacgaagtagaagaggaagtgggccaagccattagaagca agattgaagacggcactgtgaagagagaagatatattctatacttcaaagctttggagcactttcca tagaccagagctggtccgaacttgcttggaaaagacactgaaaagcactcaactgctatggtgg atctttatattattcatttcccaatggattgcagcctggagatatattttccccacgagatgagcatgg aaaactattgtttgaaacagtggatatctgtgacacatggaggccatggagaagtgtaaggatgc aggattggccaagtctattggggtgtccaactttaactgcaggcagctggagaggattctgaataa gccagggctcaaatacaagcctgtgtgcaaccaggtggaatgtcacctttatctcaaccagagca aaatgctggactattgtaagtcaaaagacatcattctggtttcctactgcacgctgggaagttcacg agacaaaacatgggtggatcagaaaagtccagttctcctagatgatccagttctttgtgccatagca aagaagtacaagcaaaccccagccctagttgcccttcgctaccagctgcagcgtggggttgtgcc cctgatcaggagtttcaacgcgaagcggatcaaagagctaacacaggttttttgaattccagttggc ttcagaggacatgaaagccctggatggtgaacagaaatttcagatacaacaatgcaaaatattttt gatgaccatcccaatcatccatttactgatgaatag |
| 5 | Signal peptide | MIRSKKLWISLLFALTLIFTMAFSNMSVQA |
| 6 | aprE version 1 Signal peptide | atgcgttcaaaaaaactttggatctctcttcttttcgctcttacacttatcttcacaatggctttctcaaac atgtctgttcaagcg |
| 7 | SP-3α-HSD | MIRSKKLWISLLFALTLIFTMAFSNMSVQAMDSISLRVALNDG NFIPVLGFGTTVPEKVAKDEVIKAKIAIDNGFRHFDSAYLYEV EEEVGQAIRSKIEDGTVKREDIFYTSKLWSTFHRPELVRTCLE KTLKSTQQDYVDLYIIHFPMALQPGDIFFPRDEHGKLLFETVD ICDTWEAMEKCKDAGLAKSIGVSNFNCRQLERILNKPGLKYK PVCNQVECHLYLNQSKMLDYCKSKDIILVSYCTLGSSRDKTW VDQKSPVLLDDPVLCAIAKKYKQTPALVALRYQLQRGVVPLI RSFKPKRIKEPTQVFEFQLASEDMKALDGLNRNFRYNNAKYF DDHPNHPFTDE |
| 8 | SP-3α-HSD nucleotide sequence | atgcgttcaaaaaaactttggatctctcttcttttcgctcttacacttatcttcacaatggctttctcaaa catgtctgttcaagcgatggattccatatctctgcgtgtagcactaaatgatggtaacttcattcctg tactggggtttggaaccactgtgcctgagaaggttgctaaggatgaagttatcaaggctactaaa atagctatagataatggattccgccattttgactctgcttatttgtacgaagtagaagaggaagtgg gccaagccattagaagcaagattgaagacggcactgtgaagagagaagatatattctatacttc aaagctttggagcactttccatagaccagagctggtccgaacttgcttggaaaagacactgaaa agcactcaacaggactatgtggatctttatattattcatttcccaatggctttgcagcctggagatat attttccccacgagatgagcatggaaaactattgtttgaaacagtggatatctgtgacacatggga ggccatggaaaagtgtaaggatgcaggattggccaagtctattggggtgtccaactttaactgta ggcagctggagaggattctgaataagccagggctcaaatacaagcctgtgtgcaaccaggtg gaatgtcacctttatctcaaccagagcaaaatgctggactattgtaagtcaaaagacatcattctg |

TABLE 1-continued

| SEQ ID NO: | Description | Sequence |
|---|---|---|
| | | gtttcctactgcacgctgggaagttcacgagacaaaacatgggtggatcagaaaagtccagttc<br>tcctagatgatccagttctttgtgccatagcaaagaagtacaagcaaaccccagccctagttgcc<br>cttcgctaccagcttcagcgtggggttgtgcccctgatcaggagtttcaagccgaagcggatca<br>aagagccaacacaggttttgaatttcagttggcttcagaggacatgaaagccctggatggcttg<br>aacagaaatttcagatacaacaatgcaaaatattttgatgaccatcccaatcatccatttactgatg<br>aatag |
| 9 | Glucose-6-phosphate 1-dehydrogenase (Zwf) | MAVTQTAQACDLVIFGAKGDLARRKLLPSLYQLEKAGQLNP<br>DTRIIGVGRADWDKAAYTKVVREALETFMKETIDEGLWDTL<br>SARLDFCNLDVNDTAAFSRLGAMLDQKNRITINYFAMPPSTF<br>GAICKGLGEAKLNAKPARVVMEKPLGTSLATSQEINDQVGE<br>YFEECQVYRIDHYLGKETVLNLLALRFANSLFVNNWDNRTID<br>HVEITVAEEVGIEGRWGYFDKAGQMIRDMIQNHLLQILCMIA<br>MSPPSDLSADSIRDEKVKVLKSLRRIDRSNVREKTVRGQYTA<br>GFAQGKKVPGYLEEEGANKSSNTETFVAIRVDIDNWRWAGV<br>PFYLRTGKRLPTKCSEVVVYFKTPELNLFKESWQDLPQNKLTI<br>RLQPDEGVDIQVLNKVPGLDHKHNLQITKLDLSYSETFNQTH<br>LADAYERLLLETMRGIQALFVRRDEVEEAWKWVDSITEAWA<br>MDNDAPKPYQAGTWGPVASVAMITRDGRSWNEFE |
| 10 | Signal peptide | MKKNTLLKVGLCVSLLGTTQFVSTISSVQA |
| 11 | Signal peptide | MKLAACFLTLLPGFAVA |
| 12 | Signal peptide | MNDLNDFLKTILLSFIFFLLLSLPTVAEA |
| 13 | Signal peptide | MKKLAIMAAASMVFAVSSAHA |
| 14 | Signal peptide | MKLKFISMAVFSALTLGVATNAS |
| 15 | Signal peptide | MRTLQGWLLPVFMLPMAVYA |

Enzymatic Activity Assay:

Verification of enzymatic activity of 3αHSD was carried out by measurement of decrease in NADPH fluorescence over time in presence of DHT. The assay was carried out as follows:

Overnight starter grown in the presence of 100 mg/ml Kan/Amp were inoculated in a fresh LB media and grown to OD 600 of 0.6, and re-suspended in BA low-growth medium. IPTG was added to a final concentration of 1 mM, and culture was placed in shaker for an additional 2-3 hours at 37 degrees. Next, culture was centrifuged for one minute, and pellet was re-suspended in 1 ml phosphate buffer (PBS) pH=7.4. To lyse cells, the pellet was sonicated at 20% amplitude 3 cycles of: 5 sec sonication and 30 sec on ice. Membrane and cell lysate/cytoplasm fraction were separated by centrifugation at 12000 RPM for ten minutes.

To assay enzymatic activity, 170 µl of the cell lysate supernatant was pipetted into each well of a 96-wells plate. To each well, NADPH (Sigma-Aldrich, 1.5 mM stock solution, made by dilution of powder purchased in 0.01N NaOH) was added to a final concentration of 150 µM. Plates were then incubated at 37° C. for 30 minutes. Fluorescence measurements were made on a Tecan Infinite 200 Pro plate reader every 1 min for 5 hours using 340/460 nm ex/em. Finally, DHT (Sigma-Aldrich, 1 mM stock solution, made by dilution of 1 mg/ml in methanol) was added to a final concentration 50 µM, and the measurement was repeated every minute for three hours.

Secretion Assay in *B. Subtilis*:

The following procedure was used to verify the activity of a signal peptide in *B. subtilis* by measurement of mCherry fluorescence in extracellular medium. Overnight cultures of *B. subtilis* with SP-mCherry and mCherry were grown in 5 ml LB+spectinomycin and incubated at 37° C. overnight (16 hr). The culture was re-suspended in 50 ml LB+50 µl spectinomycin in 250 ml Erlenmeyer and grown to OD600 of 0.6. Culture was centrifuged for 5' at 5000 g and re-suspended in bioassay medium (BA) with 0.1 mM IPTG added. 200 µl of each sample was then deposited in duplicates in a 96-wells plate, and fluorescence measurements were taken using a Tecan M100 plate reader use a 560 ex/610 em.

Enzymatic Activity Assay for Screening Single Colonies of Chimeric Peptides Described in Example 4:

Verification of enzymatic activity of 3αHSD was carried out by measurement of decrease in NADPH fluorescence over time in presence of DHT. The assay was carried out as follows:

Each colony was plated from a glycerol stock on a Kanamycin selective agar plate, incubate overnight. A stock medium of (5-10) % LB in BA, 10 ul/ml Kanamycin was prepared. each single colony was inoculated with 2 ml of the prepared growth medium and grow for 24-48 hours. Next, cell supernatants were obtained by centrifugation for 20 min in max speed.

Next, 200 µl of supernatant, duplicate for each condition were added to a 96-wells microplate which was kept on ice. Each duplicate of a colony was treated with 0 or 200 µM of NADPH and 0 or 150 uM DHT. Finally, the plate was placed in a plate reader for 2-5 hours at 37° C. and fluorescence was measure every 1 minute at 340 nm excitation, 450 nm emission.

Western Blotting:

Control proteins were run on SDS-PAGE in order to determine the conditions for the experiment (results not shown). Briefly, it was chosen to concentrate the cell supernatant using size exclusions columns (Merck). Cell lysate were collected after the cells underwent a standard sonication protocol. Western blotting was performed according to standard protocols.

Example 1

AKR1C9 Expression and 3α-HSD Activity in E. Coli

Figure 1B:
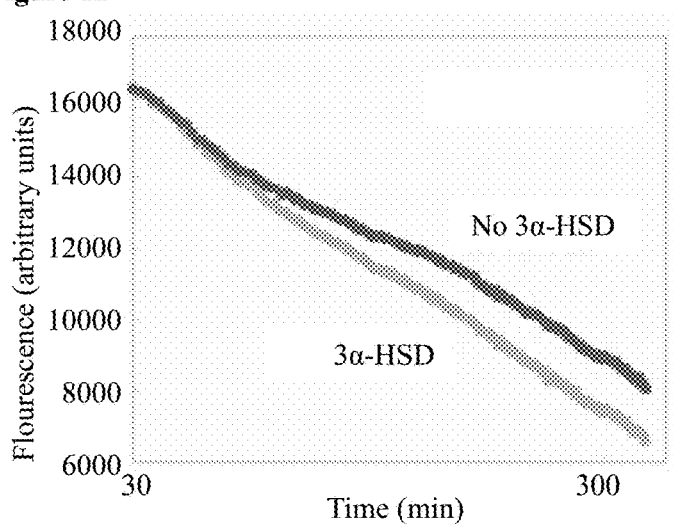
FIG. 1B: is a graph showing NADPH degradation rate over time in logarithmic scale with initial concentration of 40 µM DHT.

In order to quantify the 3α-HSD enzymatic activity (FIG. 1A), one would ideally track the degradation of its substrate DHT. However, since there is no known assay for DHT detection, 3α-HSD enzymatic activity was assayed by tracking the degradation of its cofactor, NADPH. NADPH concentration can be quantified using fluorescence due to its excitation and emission curves which peak at 340 nm and at 460 nm respectively. To get an estimate for the kinetics of 3α-HSD enzymatic reaction, the effect of increasing the initial substrate concentration (DHT) was examined. E. coli BL21 cells containing the AKR1C9 gene construct were sonicated after two hours of induction with IPTG, 150 µM NADPH was added to the lysates in a 96-wells plate, and inserted into a plate reader pre-heated to 37° C. for 30 minutes to allow for result stabilization (37° C. is in the optimal temperature range for the enzyme activity). In previous experiments, fluctuations in fluorescence during the first 15-30 minutes after the addition of NADPH were observed, even in negative controls. These fluctuations may occur due to a reaction of NADPH with the phosphate buffer, resulting in a new equilibrium state between NADPH and NADP+. Therefore, DHT was added after 30 minutes to each well in various concentrations and measured NADPH fluorescence over the subsequent 5.5 hours. FIG. 1B shows the results for lysate with and without 3αHSD. The plot shows that on a logarithmic time scale both lysates exhibit a relatively linear reduction in fluorescence levels as a function of time. However, the lysate containing 3αHSD exhibits a linear decline with a steeper slope indicating that the reduction in NADPH concentration is occurring at a higher rate for this strain. This observation is consistent with a faster NADPH degradation rate due to the specific enzymatic activity.

Figure 1C:
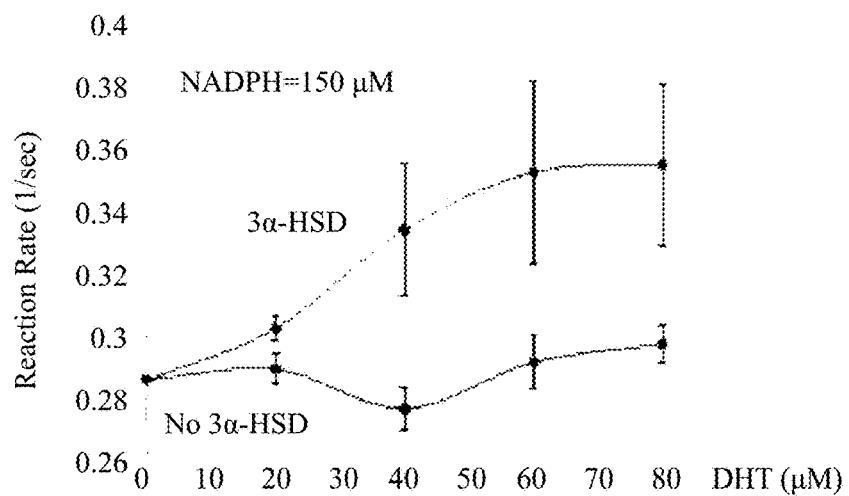
FIG. 1C: is a graph showing reaction rate vs. DHT concentration.

To obtain an estimate of the over-all enzymatic activity, the putative NADPH degradation rate for several DHT concentrations was measured. The results of the slopes from each degradation curve are shown in FIG. 1C. The plot shows that the reaction rate in the absence of 3α-HSD enzyme stays relatively constant with increasing DHT concentrations, whereas it rises by about 25% (from 0.285 sec$^{-1}$ to 0.36 sec$^{-1}$) in the presence of the enzyme. Therefore, this data suggests that the enzymatic reaction rate reaches saturation at a DHT concentration above 60 µM.

Figure 1D:
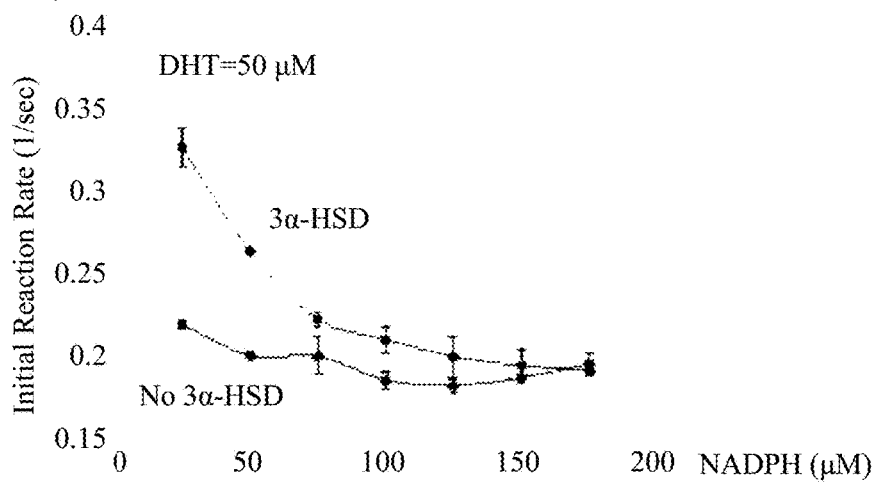
FIG. 1D: is a graph showing reaction rate vs. NADPH concentration.

Next NADPH degradation rate dependence on its initial concentration was evaluated. This was done using the same assay with a constant DHT concentration of 50 µM, and varying NADPH concentrations. In the plot (FIG. 1D), a decrease in the reaction rate with increasing initial NADPH concentration was observed in presence of 3α-HSD enzyme (orange line), while the lysate that does not contain the 3α-HSD enzyme did not exhibit a dependence on initial NADPH concentration. One possible explanation for the declining initial co-factor concentration dependency, is that during the 30 minutes of stabilization, some fraction of the NADPH molecules was converted to NADP+ by other enzymes from the lysate, which then could bind to 3α-HSD and inhibit its activity. It is possible that in high concentration of NADPH, after 30 minutes, a saturating fraction of the 3α-HSD molecules are bound to NADP+ and hence the reaction in the direction of DHT reduction is inhibited.

Example 2

Modeling 3α-HSD Kinetics and NADPH Degradation

NADPH degradation was modeled based on a simple two-ligand-receptor thermodynamic model coupled to a rate equation mechanism, where the receptor has two ligand binding pockets. This sort of model has been used in the past to model enzymatic reactions, and is adequate for exploring the phase space of behaviors for co-factor based catalysis of DHT by 3α-HSD.

Figure 2A:
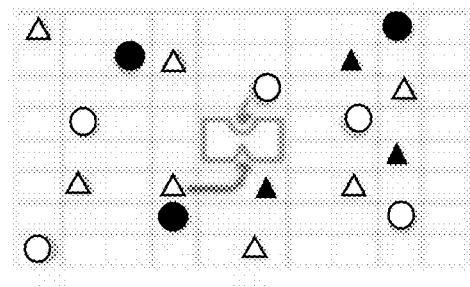
FIG. 2A: is a model for NADPH concentration as a function of time with and without the presence of the catalytic enzyme.
Figure 2B:
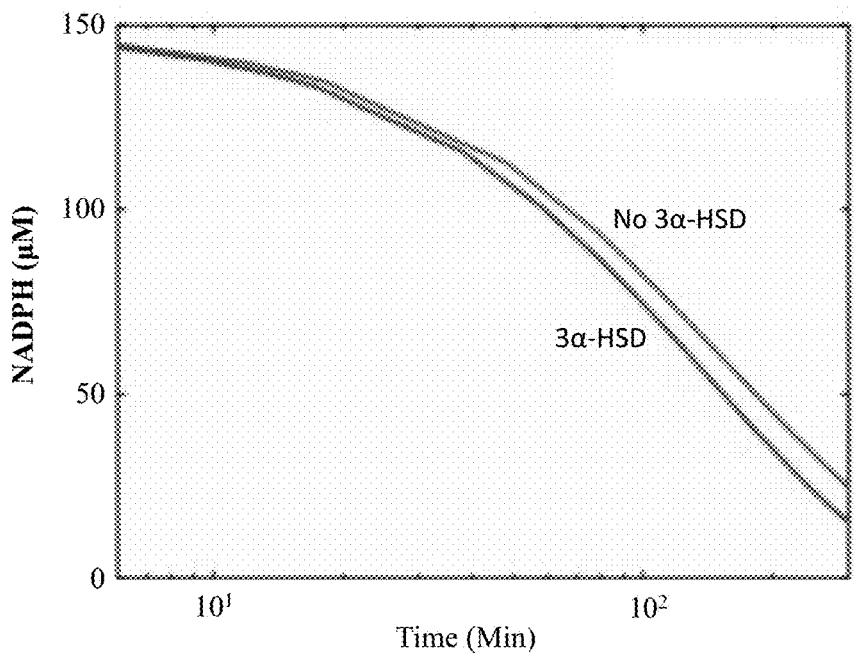
FIG. 2B: is a graph showing model prediction for NADPH concentration as a function of time with and without the present of the catalytic enzyme.

In brief, the model posits a four-state ligand-receptor system, where the only enzymatically active state is the one with the receptor bound by both ligand and co-factor (See FIG. 2A for model schematic). Using this model, equations for DHT and NADPH degradation were generated. These equations are then used to model the evolution of DHT and NADPH concentration over time as the enzymatic reaction proceeds. FIG. 2B presents the model's prediction for NADPH concentration as a function of time using a set of parameters obtained from the literature. NADPH naturally degrades to NADP with some rate leading to the exponentially decaying a curve. With the enzyme present, the exponential decay of the concentration becomes steeper indicating a faster rate of degradation. This prediction is consistent with what was actually observed for the experiment and plotted in FIG. 1B-C.

Figure 2C:
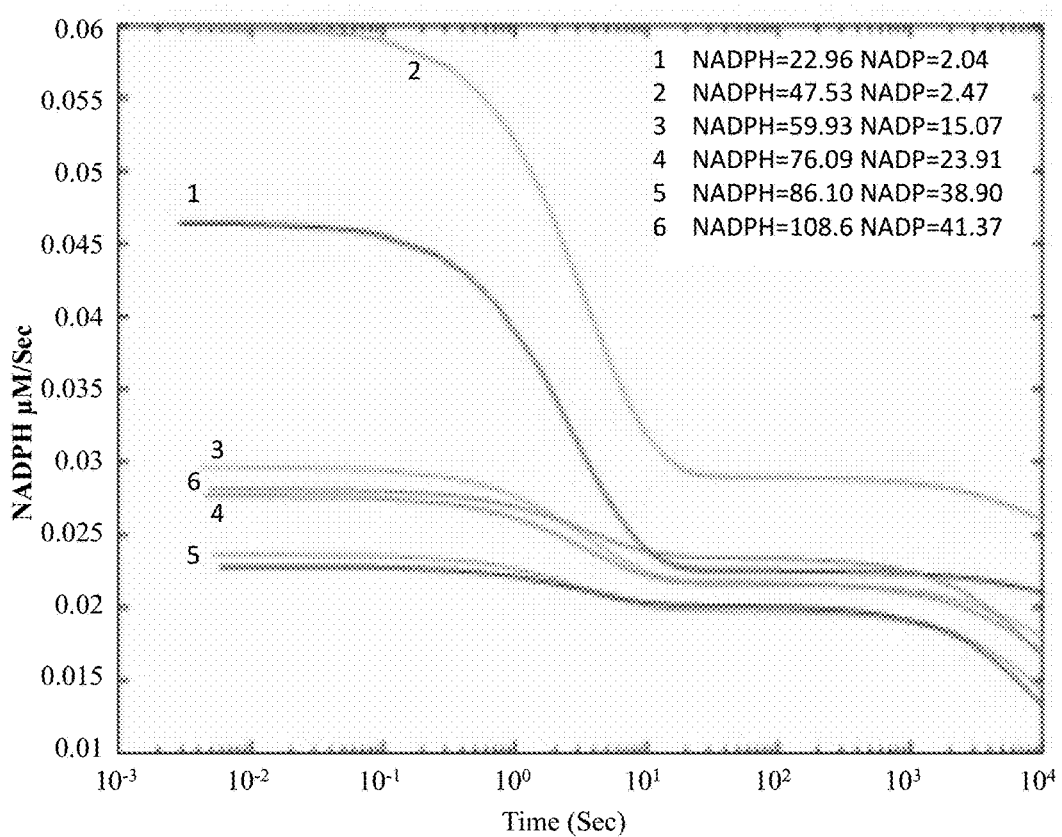
FIG. 2C: presents model predictions for the rate of NADPH degradation as a function of time for several initial concentrations of NADPH and NADP.

To model the inverse dependence of the degradation rate on initial co-factor concentration the model was tested with various initial conditions (FIG. 2C). Here the figure shows that as the initial NADPH concentration is low the rate of degradation starts at a much higher value, which rapidly decays to a steady state value. On the other hand, when the initial concentration of NADPH is higher, the degradation rate remains more or less constant over time at a lower value, which is similar to the natural degradation rate. In this case, the model predicts that a high initial concentration of NADPH produces a higher titer of NADP from natural non-enzymatic degradation processes, which in turn saturate the active site on the enzyme. This in turn deactivates the enzyme leading to the lower degradation rates. The results shown in FIG. 2B are consistent with the trend shown in FIG. 1D. Consequently, the model's agreement with the data supports the fact that the assay accurately tracks NADPH measurements, and as a result reflects an accurate depiction of 3α-HSD enzymatic activity.

Example 3

Expression and Secretion of mCherry Reporter Gene in B. Subtilis

Next, the option of directing secretion of 3α-HSD enzyme using one of B. subtilis' well-characterized secretion systems was explored. In these systems, the bacteria typically encode a secretion signal peptide (SP) directly up-stream of the target gene, hence producing a chimeric polypeptide with the SP fused to the N-terminus of the secreted enzyme. The signal peptide associated with gene aprE was used. AprE encodes an extracellular alkaline-serine protease (subtilisin E), which is the most abundant protease secreted to the medium in wildtype B. subtilis. By fusing only the portion of aprE which encodes for the secretion peptide to the 3α-HSD gene, the chimeric protein product should be recognized by the secretion system of the protease and secreted into the extracellular medium at a relatively high titer. This design effectively allows "hijacking" the subtilisin E secretion pathway, for the purpose of generating a sustainable microbial production facility.

Figure 3A:
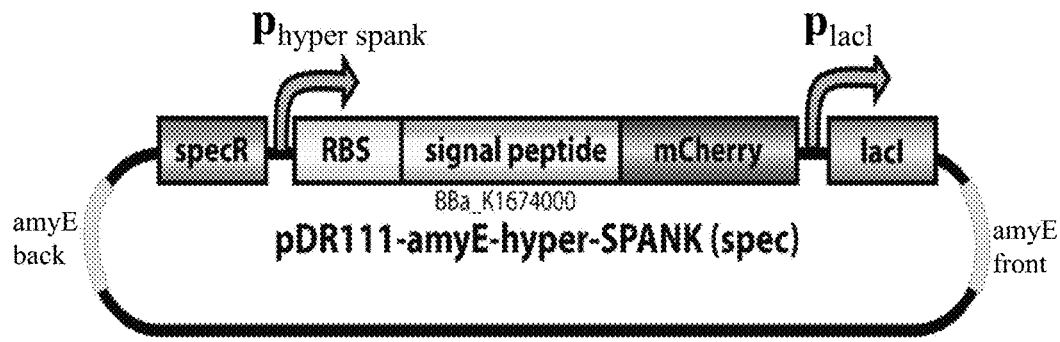
FIG. 3A: presents Circuit diagram for the secreted and non-secreted mCherry proteins used in the experiments.
Figure 3B:
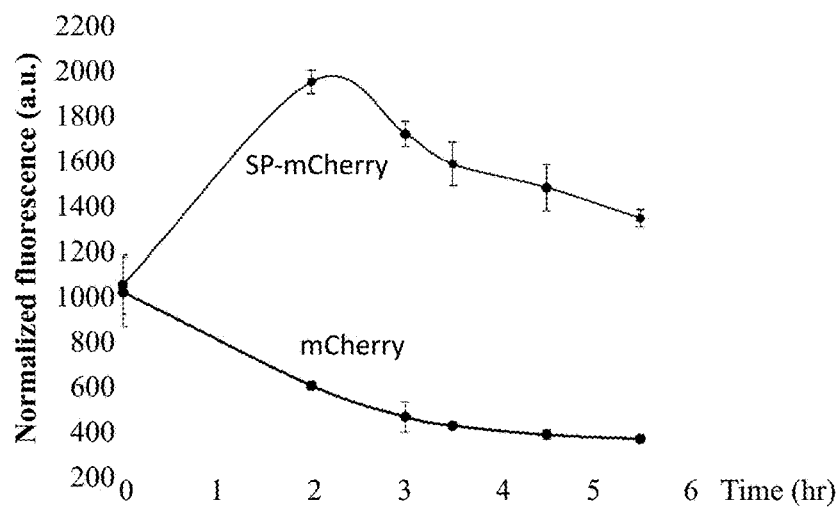
FIG. 3B: is a graph showing normalized fluorescence of the supernatant vs. Time for *B. subtilis* strains expressing SP-mCherry and mCherry.

To test this approach, the portion encoding for the signal peptide of AprE was initially cloned directly upstream of the fluorescent reporter mCherry (SP-mCherry). The chimeric gene was placed under the control of the *B. subtilis* hyperspank promoter, and a ribosome binding site from the iGEM registry—BBa_K143021 BioBrick was added as well to ensure a high expression level. (FIG. 3A). To check for fluorescent protein secretion, two *B. subtilis* strains were used: one containing the gene for the mCherry protein and one with the signal peptide-mCherry fusion protein. The strains were initially grown in LB to OD600 value of 0.6, and then were resuspended in low growth media buffer, and induced by 0.1 mM of IPTG. Next, 200 μl of the culture was centrifuged at each hour after induction, and the supernatant was assayed for fluorescence activity. The results are shown in FIG. 3B. The data shows that the fluorescence of the supernatant of the strain containing only mCherry decreases over time, whereas the fluorescence of the supernatant of the strain containing mCherry fused to signal peptide initially showed an increase in fluorescence over time until reaching a maximum, and then followed by a slow decrease over time. The increase in fluorescence seen in the graph of SP-mCherry suggests that the chimeric protein is secreted to the growth medium during the induction period, as expected. The decrease following that maxima is probably due to a slowing of the *B. subtilis* growth rate and over-all gene expression due to the low-growth media buffer.

Figure 3C:
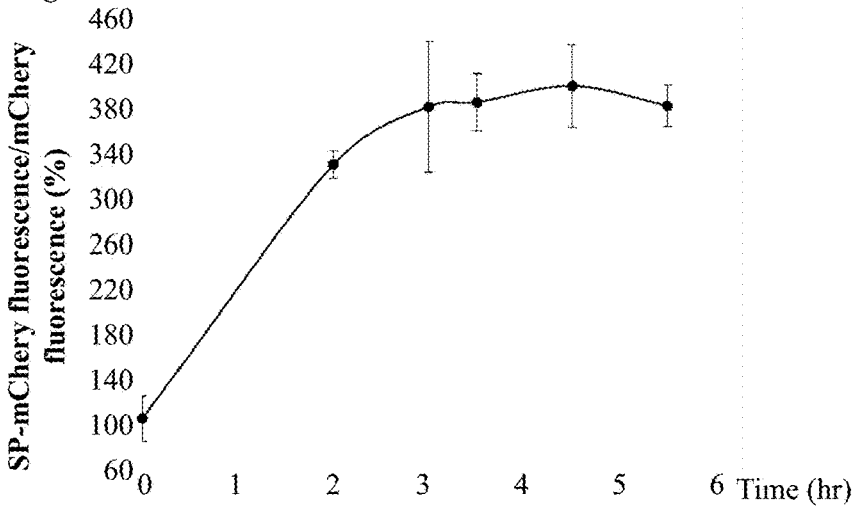
FIG. 3C: is a graph showing supernatant fluorescence ratio of SP-mCherry fusion to mCherry as a function of time after induction by IPTG.

To evaluate the efficacy of mCherry secretion, the ratio of the fluorescence measurements of the strain expression SP-mCherry was compared to the one expressing the native mCherry fluorescent protein was plotted (FIG. 3C). The data shows that the fluorescence measurement obtained for the supernatant with SP-mCherry is about 300% higher, relative to the fluorescence observed from the mCherry supernatant alone (with no signal peptide) starting from about two hours after induction to the end of the experiment.

Figure 3D:
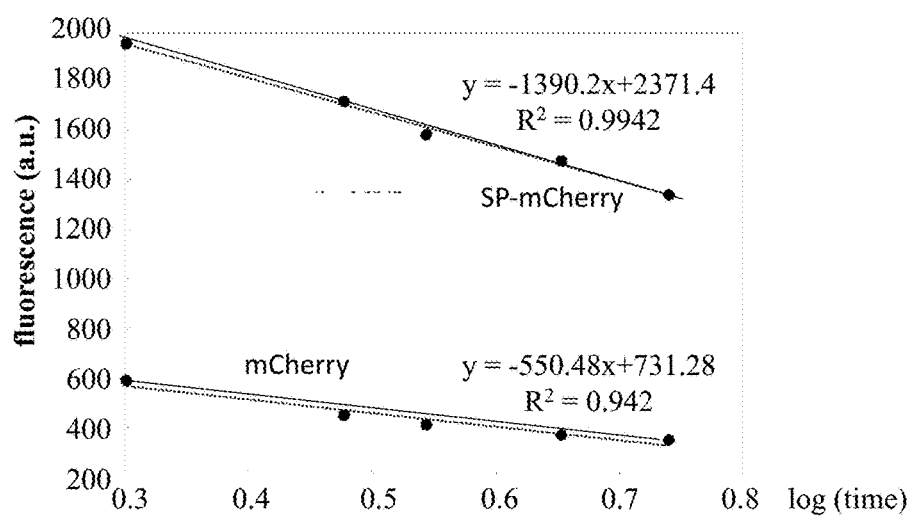
FIG. 3D: is a graph showing mCherry degradation rate (logarithmic time scale) after reaching fluorescence maxima.

A closer look at FIG. 3B indicates that while SP-mCherry is indeed present at higher titers in the supernatant, it also degrades faster. To show this, fluorescence data (after reaching their respective maxima) as a function of time, was plotted on logarithmic time-scale (FIG. 3D). The graph shows that while both fluorescence measurements fall on a straight line, the data for SP-mCherry can be fitted by a line with a steeper slope, which indicates a significantly faster degradation rate as compared with the native mCherry. This increased degradation rate of SP-mCherry can be induced by the secretion peptide itself, as it may also form a target for secreted proteases in the extra-cellular media.

Example 4

Signal Peptide Screening

In order to identify signal peptides suitable for secretion of 3α-HSD, chimeric proteins, each consisted of 3α-HSD fused to a signal peptide (SP) from a library of 173 domains from SEC, TAT and unknown secretion pathways were produced. The chimeric peptides were screened and for each chimeric peptide the expression and secretion of 3α-HSD was evaluated. The presence of 3α-HSD was measured indirectly, by measurement of decrease in NADPH fluorescence over time in presence of dihydrotestosterone (DHT). By comparing 3α-HSD activity, the best possible secretion signals for 3α-HSD were selected.

A g-block DNA fragment was ordered from IDT, containing the akrlc14 variant of the 3α-HSD gene (a gene synonym to akrlc9 which has the amino acid sequence as set forth in SEQ ID NO: 3 and encoded by the nucleic acid sequence as set forth in SEQ ID NO: 4). The gene was then incorporated to pBE-S plasmid, introduced with a mix of 173 signal peptides (ordered from Takara) and transformed into STELLAR competent *e-coli* cells to create a library with a high copy number of plasmid DNA. The resulting 1960 colonies were scraped from the agar plates and a MIDI prep protocol was performed to achieve a high DNA concentration with high complexity. This plasmid library was then transformed into *B. subtilis* RIK1285 (ordered from Takara), yielding 1152 colonies.

Fluorescence measurements were plotted on a graph (fluorescence as a function of time), and the linear slope of each graph received from 10 min into the reaction until 55 min into the reaction was calculated. This slope is a direct indicator for the degradation rate of NADPH in the cells supernatant. Further, NADPH degradation rate is an indicator of secreted 3α-HSD activity in the *Bacillus subtilis* cells.

Figure 4A:
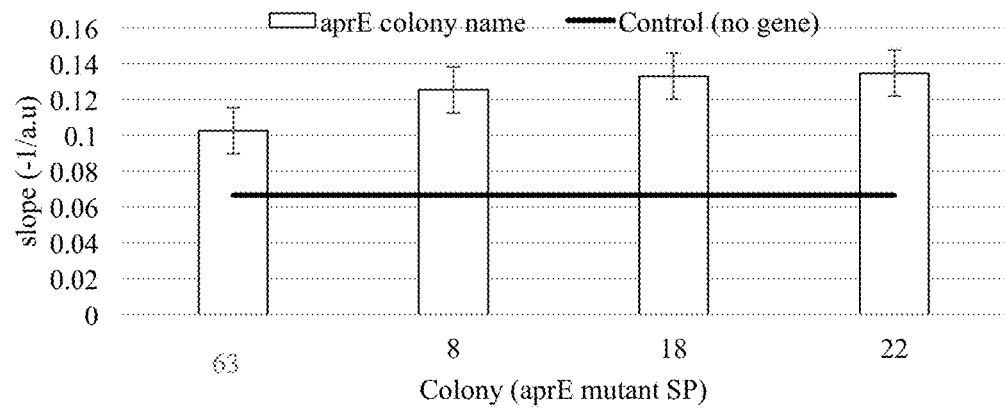
FIG. 4A: is a bar graph showing average slope (indicator for enzymatic activity) for mutant-aprE screened colonies (backbone plasmid).

Multiple colonies contained a mutant-aprE signal peptide were found, but with varying levels of 3α-HSD secretion. FIG. 4A is a graph demonstrating the slope of NADPH degradation of four such colonies (See Table 2 for sequences). The slopes are compared with the baseline of control cells (cells without the 3α-HSD gene inserted, 4 duplicates—black line). The resulting rate of NADPH consumption is higher for this SP-variant as compared with the control by about 3σ with an average NADPH breakdown rate measured for these four colonies of 0.1239±0.0128 (1/sec).

Figure 4B:
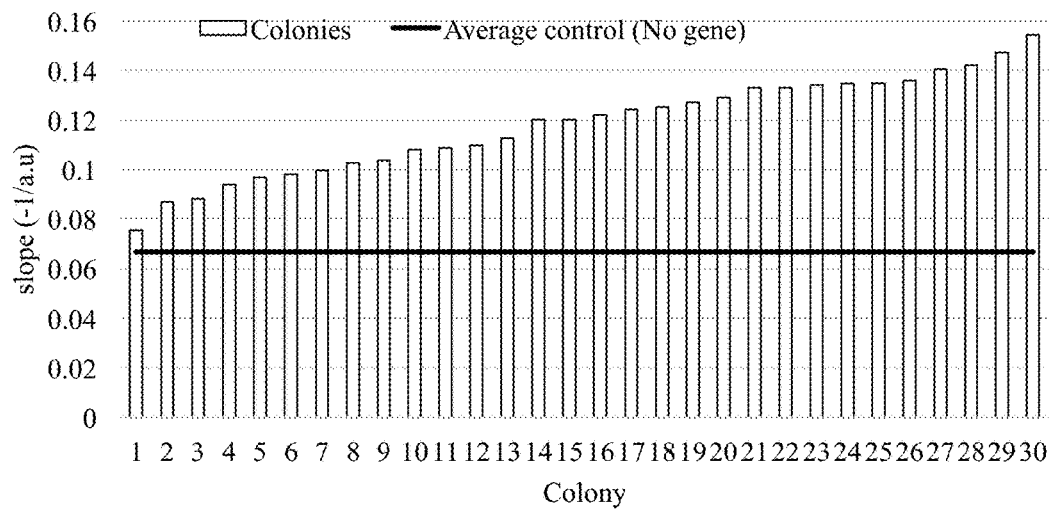
FIG. 4B: is a bar graph showing average slope for different screened colonies.
Figure 4C:
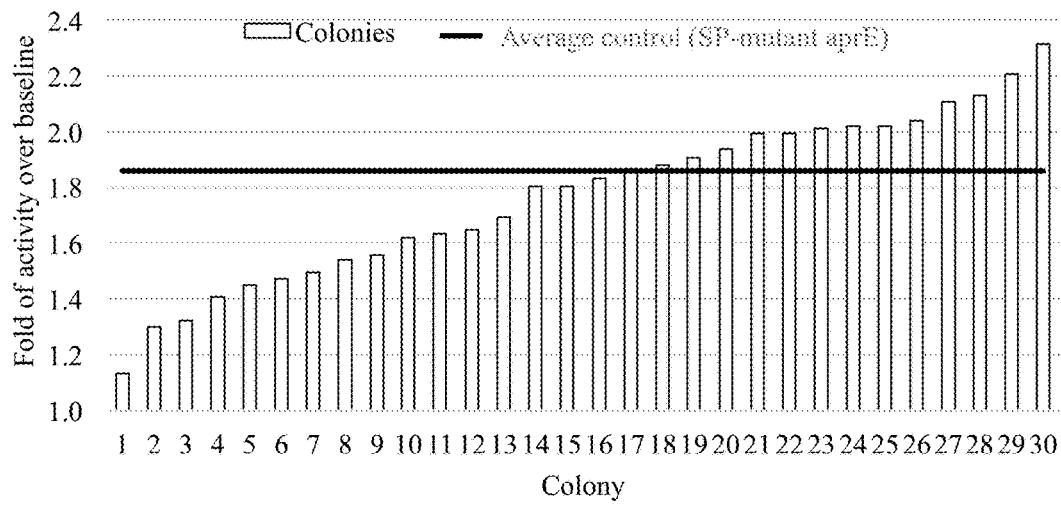
FIG. 4C: is a bar graph showing a fold of slope increase as compared to the mutant-aprE average.

The slope for the NADPH consumption rate was measured for every colony that was screened, and the first 30 colonies were compared with the baseline of the control cells (FIG. 4B). Results demonstrated a distribution of consumption rates from values near that of the control, indicating no likely secretion, to significantly larger rates (right most bars) that indicate even more efficient secretion than that obtained with the mutant aprE. The mean rates obtained for the two most efficient colonies are >6σ away from the control mean. Finally, NADPH degradation for the 30 first colonies was compared with the average of all mutant aprE signal peptide colonies (FIG. 4C). The highest NADPH degradation rate was achieved for colony number 30, higher by 231.5% from the no 3α-HSD control and by 80.3% from mutant-aprE SP average. DNA sequencing was performed for the colonies with the highest measured rate of NADPH degradation, and further colonies were examined in an effort to find superior SPs. In Table 2, the amino acid and DNA sequence of the signal peptides of these colonies are shown. In addition, sequencing results confirmed that no 3α-HSD gene was inserted into the control *B. subtilis* RIK1285 cells (contained an empty pBE-S plasmid).

TABLE 2

Sequences from the screened colonies

| # colony | slope (-1/a.u) | ΔFold | Sequence of signal peptide (SEQ ID NO) | aa sequence of SP (SEQ ID NO) | SP name |
|---|---|---|---|---|---|
| negative control (no 3αHSD) | 0.0838 | 1 | GTGAGAAGCAAAAAATTGTGGATCAGCTTGTTGTTTGCGTTAACGTTAATCTTTACGATGGCGTTCAGCAACATGTCTGCGCAGGCT (46) | VRSKKLWISLLFALTLIFTMAFSNMSAQA (16) | aprE version 2 |
| 30 | 0.1927 | 2.3 | ATGTTGAAGAAAGTCATTTTAGCCGCTTTTATCTTAGTAGGAAGTACTTTGGGAGCTTTTAGTTTTTCATCAGATGCCAGTGCG (47) | MLKKVILAAFILVGSTLGAFSFSSDASA (17) | Uncharacterized protein YdjM |
| 31 | 0.1854 | 2.2 | ATGAAAAAGAAACAAGTAATGCTCGCTTTAACAGCTGCCGCAGGACTGGGTTTGACAGCACTTCATTCCGCTCCCGCAGCAAAAGCT (48) | MKKKQVMLALTAAAGLGLTALHSAPAAKA (18) | yfhK |
| 28 | 0.1759 | 2.1 | ATGAAAAAAGAATTACTTGCTTCACTAGTTTTATGTCTATCATTGTCACCATTAGTGTCAACAAATGAAGTTTTTGCA (49) | MKKELLASLVLCLSLSPLVSTNEVFA (19) | yjcM |
| 27 | 0.1759 | 2.1 | ATGACAAAAAAAGCATGGTTTCTGCCGCTCGTCTGTGTATTACTGATTTCCGGATGGCTTGCGCCAGCAGCTTCAGCAAGCGCG (50) | MTKKAWFLPLVCVLLISGWLAPAASASA (20) | Uncharacterized protein |
| 26 | 0.1676 | 2 | ATGAAGTTGAAAACTAAAGCGTCAATAAAATTCGGAATATGTGTTGGGCTTTTATGTTTAAGCATTACTGGTTTCACACCTTTTTTCAACTCAACACATGCCGAAGCA (51) | MKLKTKASIKFGICVGLLCLSITGFTPFFNSTHAEA (21) | Beta-lactamase |
| 24 | 0.1676 | 2 | GTGAGAAGCAAAAAATTGTGGATCAGCTTGTTGTTTGCGTTAACGTTAATCTTTACGATGGCGTTCAGCAACATGTCTGCGCAGGCT (46) | VRSKKLWISLLFALTLIFTMAFSNMSAQA (16) | aprE version 2 |
| 22 | 0.1676 | 2 | GTGAGAAGCAAAAAATTGTGGATCAGCTTGTTGTTTGCGTTAACGTTAATCTTTACGATGGCGTTCAGCAACATGTCTGCGCAGGCT (46) | VRSKKLWISLLFALTLIFTMAFSNMSAQA (16) | aprE version 2 |
| 21 | 0.1676 | 2 | ATGAAGAAAGCATTTATTTTATCTGCTGCCGCTGCGGTTGGATTATTCACATTCGGGGGCGTACAGCAAGCATCAGCG (52) | MKKAFILSAAAVGLFTFGGVQQASA (22) | YkwD |
| 32 | 0.1672 | 2.0 | ATGATGAAAAAGCTATTTCATTCCACACTTATTGTGGTTGTTATTCTTTAGTTTTTTCGGCGTTCAGCCCATCCACGCG (53) | MMKKLFHSTLIVLLFFSFFGVQPIHA (23) | yfkD |
| 33 | 0.1664 | 2.0 | ATGGGTATGAAAAAGAAATTGAGTTTAGGAGTTGCTTCTGCAGCACTAGGATTAGCTTTAGTTGGAGGAGGAACATGGGCA (54) | MGMKKKLSLGVASAALGLALVGGGTWA (24) | tasA |
| 34 | 0.1641 | 2.0 | ATGAAGTCCAAAGGATCGATTATGGCATGTCTCA | MKSKGSIMACLILFSFTITTFIN | sleB |

TABLE 2-continued

Sequences from the screened colonies

| # colony | slope (-1/a.u) | ΔFold | Sequence of signal peptide (SEQ ID NO) | aa sequence of SP (SEQ ID NO) | SP name |
|---|---|---|---|---|---|
| | | | TCCTTTTTTCCTTTACAA TAACGACGTTTATTAAT ACTGAAACGATCTCTGC CTTTTCG (55) | TETISAFS (25) | |
| 18 | 0.1592 | 1.9 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |
| 35 | 0.1633 | 1.9 | ATGAAAAAAAAAAAA GGCGAAACTTTAAAAGG TTCATTGCAGCATTTTTA GTGTTGGCTTTAATGAT TTCATTAGTGCCAGCCG ATGTACTAGCA (56) | MKKKKRRNFK RFIAAFLVLAL MISLVPADVLA (26) | wapA |
| 36 | 0.1612 | 1.9 | ATGAATCAAATGAAAGA TACAATATTGCTCGCCG GTCTCGGATTGATAGGC GGTTCGATTGCCCTAGC C (57) | MNQMKDTILL AGLGLIGGSIA LA (27) | tyrA |
| 37 | 0.1583 | 1.9 | ATGGATAAATTCTTAAA CAACCGCTGGGCTGTGA AAATTATTGCTCTGCTTT TCgCGCTCTTGCTTTATG TGGCGGTTAACAGC (58) | MDKFLNNRWA VKIIALLFALLL YVAVNS (28) | ybbR |
| 38 | 0.1581 | 1.9 | ATGAAAAAGAAAACTA AAATTATACTTTCTCTCT TGGCAGCACTTATTGTT ATATTGATAGTACTTCC AGTTCTATCTCCTGTTGT CTTTACAGCTTCTTCG (59) | MKKKTKIILSL LAALIVILIVLP VLSPVVFTASS (29) | yjcN |
| 14 | 0.1508 | 1.8 | ATGAAGAAGAGGCTAAT CGGATTTTTGGTCTTAGT TCCTGCTTTGATTATGTC AGGTATTACTTTAATCG AAGCA (60) | MKKRLIGFLVL VPALIMSGITLI EA (30) | SPBc2 prophage- derived uncharact- erized protein YolC |
| 39 | 0.1544 | 1.8 | ATGTTGAAGAAAGTCAT TTTAGCCGCTTTTATCTT AGTAGGAAGTACTTTGG GAGCTTTTAGTTTTTCAT CAGATGCCAGTGCG (47) | MLKKVILAAFI LVGSTLGAFSF SSDASA (17) | ydjM |
| 40 | 0.1475 | 1.8 | ATGAAAAGACTGTTTAT GAAGGCTTCATTGGTGT TATTCGCAGTAGTATTT GTTTTTGCCGTCAAAGG TGCACCCGCCAAGGCG (61) | MKRLFMKASL VLFAVVFVFAV KGAPAKA (31) | yjfA |
| 13 | 0.1424 | 1.7 | ATGACAAAAAAAGCAT GGTTTCTGCCGCTCGTCT GTGTATTACTGATTTCC GGATGGCTTGCGCCAGC AGCTTCAGCAAGCGCG (50) | MTKKAWFLPL VCVLLISGWLA PAASASA (20) | Uncharact- erized protein |
| 41 | 0.1463 | 1.7 | ATGAAAAAGAGACTGAT TCAAGTCATGATCATGT TCACCCTGCTGTTGACtA TGGCATTTTCGGCAGAT GCA (62) | MKKRLIQVMI MFTLLLTMAFS ADA (32) | sacC |
| 42 | 0.1406 | 1.7 | ATGACAAAAAAAGCAT GGTTTCTGCCGCTCGTCT | MTKKAWFLPL VCVLLISGWLA | yurI |

TABLE 2-continued

Sequences from the screened colonies

| # colony | slope (-1/a.u) | ΔFold | Sequence of signal peptide (SEQ ID NO) | aa sequence of SP (SEQ ID NO) | SP name |
|---|---|---|---|---|---|
| | | | GTGTATTACTGATTTCC GGATGGCTTGCGCCAGC AGCTTCAGCAAGCGCG (50) | PAASASA (20) | |
| 43 | 0.136 | 1.6 | ATGAAGTTGAAAACTAA AGCGTCAATAAAATTCG GAATATGTGTTGGGCTT TTATGTTTAAGCATTACT GGTTTCACACCTTTTTTC AACTCAACACATGCCGA AGCA (51) | MKLKTKASIKF GICVGLLCLSIT GFTPFFNSTHA EA (21) | penP |
| 44 | 0.1348 | 1.6 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |
| 45 | 0.1348 | 1.6 | ATGTCCGGCAAAAAGAA AGAATCAGGTAAGTTCC GTTCGGTTTTGCTTATCA TTATCCTCCCGCTGATGT TTCTATTAATCGCAGGG GGGATTGTTCTTTGGGC TGCTGGT (63) | MSGKKKESGK FRSVLLIIILPL MFLLIAGGIVL WAAG (33) | ylxF |
| 46 | 0.1342 | 1.6 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |
| 12 | 0.1340 | 1.6 | ATGAAAAAGCGTTTTTT CGGTCCAATTATTTTGG CGTTTATTCTATTCGCAG GCGCCATCGCAGCG (64) | MKKRFFGPIIL AFILFAGAIAA (34) | Protein DltD |
| 11 | 0.1340 | 1.6 | ATGTCCGGCAAAAAGAA AGAATCAGGTAAGTTCC GTTCGGTTTTGCTTATCA TTATCCTCCCGCTGATGT TTCTATTAATCGCAGGG GGGATTGTTCTTTGGGC TGCTGGT (63) | MSGKKKESGK FRSVLLIIILPL MFLLIAGGIVL WAAG (33) | FlaA locus 22.9 kDa protein |
| 47 | 0.133 | 1.6 | ATGAAGAAAGCATTTAT TTTATCTGCTGCCGCTGC GGTTGGATTATTCACAT TCGGGGGCGTACAGCAA GCATCAGCG (52) | MKKAFILSAAA AVGLFTFGGV QQASA (22) | ykwD |
| 48 | 0.1331 | 1.6 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |
| 8 | 0.1257 | 1.5 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | Subtilisin E |
| 49 | 0.1293 | 1.5 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |

TABLE 2-continued

Sequences from the screened colonies

| # colony | slope (-1/a.u) | ΔFold | Sequence of signal peptide (SEQ ID NO) | aa sequence of SP (SEQ ID NO) | SP name |
|---|---|---|---|---|---|
| 50 | 0.1273 | 1.5 | ATGAAAAAAAAATACTAAGACAAAAAGTAAGTATAATTATAAAATAAACACTATTCCCGACCTTTTCATACAATACAGCT | MKKKY*DKKVSIIIK*TLFPTFSYNTA | yrvJ |
| 51 | 0.1253 | 1.5 | GTGAGAAGCAAAAAATTGTGGATCAGCTTGTTGTTTGCGTTAACGTTAATCTTTACGATGGCGTTCAGCAACATGTCTGCGCAGGCT (46) | VRSKKLWISLLFALTLIFTMAFSNMSAQA (16) | aprE version 2 |
| 22 | 0.1243 | 1.5 | ATGTTTAAGAAACATACGATCTCTTTGCTCATTATATTTTTACTTGCGTCTGCTGTTTTAGCA (65) | MFKKHTISLLIIFLLASAVLA (35) | ydhT |
| 53 | 0.1224 | 1.5 | ATGAAAAAAATAGTGGCAGCCATCGTGGTAATCGGTCTTGTGTTTATCGCATTTTTTTATCTTTACAGCCGATCAGGCGATGTGTATCAATCGGTAGACGCG (66) | MKKIVAAIVVIGLVFIAFFYLYSRSGDVYQSVDA (36) | yhfM |
| 54 | 0.1222 | 1.5 | ATGAAAAAATTCCCGAAGAAATTACTGCCTATCGCGGTTTTATCATCAATTGCGTTCAGCAGCTTAGCCAGCGGCAGTGTGCCTGAAGCCAGCGCC (67) | MKKFPKKLLPIAVLSSIAFSSLASGSVPEASA (37) | phoB |
| 5 | 0.1173 | 1.4 | ATGAGATTCACTAAGGTAGTTGGATTTTTGTCTGTTTTAGGGTTGGCTGCGGTTTTTCCATTAACGGCACAAGCA (68) | MRFTKVVGFLSVLGLAAVFPLTAQA (38) | Uncharacterized protein |
| 55 | 0.1203 | 1.4 | ATGAGAATACAGAAAAGACGAACACACGTCGAAAACATTCTCCGTATTCTTTTGCCCCCAATTATGATACTTAGCCTAATCCTCCCAACACCACCCATTCATGCA (69) | MRIQKRRTHVENILRILLPPIMILSLILPTPPIHA (39) | yflcN |
| 56 | 0.1203 | 1.4 | ATGAAGAAGAGGCTAATCGGATTTTTGGTCTTAGTTCCTGCTTTGATTATGTCAGGTATTACTTTAATCGAAGCA (60) | MKKRLIGFLVLVPALIMSGITLIEA (30) | yolC |
| 57 | 0.1128 | 1.3 | ATGACAAAAAAAGCATGGTTTCTGCCGCTCGTCTGTGTATTACTGATTTCCGGATGGCTTGCGCCAGCAGCTTCAGCAAGCGCG (50) | MTKKAWFLPLVCVLLISGWLAPAASASA (20) | yurI |
| 58 | 0.1099 | 1.3 | ATGAAAAAGCGTTTTTTCGGTCCAATTATTTTGGCGTTTATTCTATTCGCAGGCGCCATCGCAGCG (64) | MKKRFFGPIILAFILFAGAIAA (34) | dltD |
| 59 | 0.1089 | 1.3 | ATGTCCGGCAAAAAGAAAGAATCAGGTAAGTTCCGTTCGGTTTTGCTTATCATTATCCTCCCGCTGATGTTTCTATTAATCGCAGGGGGGATTGTTCTTTGGGCTGCTGGT (63) | MSGKKKESGKFRSVLLIIILPLMFLLIAGGIVLWAAG (33) | ylxF |
| 60 | 0.108 | 1.3 | ATGATTAAAATGCAAAAAAAGAATAAATTTATGA | MIKMQKKNKFMNRGAAILSIC | pbpB |

TABLE 2-continued

Sequences from the screened colonies

| # colony | slope (-1/a.u) | ΔFold | Sequence of signal peptide (SEQ ID NO) | aa sequence of SP (SEQ ID NO) | SP name |
|---|---|---|---|---|---|
| | | | ATAGAGGAGCAGCGATT CTAAGTATTTGTTTCGCT CTCTTTTTCTTTGACATC CTGGGGAGAATGGCA (70) | FALFFFDILGR MA (40) | |
| 61 | 0.106 | 1.3 | ATGAAAAAAAATAACT TGCTTCACTAATTATAT GTCTATAATTGTAACAA TTAATGTCAACAAATGA AGTTTTTGCA | MKKK*LASLII CL*L*QLMSTN EVFA | yjcM |
| 62 | 0.1038 | 1.2 | ATGTTTAAGAAACATAC GATCTCTTTGCTCATTAT ATTTTTACTTGCGTCTGC TGTTTTAGCA (65) | MFKKHTISLLII FLLASAVLA (35) | ydhT |
| 63 | 0.1026 | 1.2 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |
| 64 | 0.0996 | 1.2 | ATGAACATCAAAAAGTT TGCAAAACAAGCAACA GTATTAACCTTTACTAC CGCACTGCTGGCAGGAG GCGCAACTCAAGCGTTT GCG (71) | MNIKKFAKQA TVLTFTTALLA GGATQAFA (41) | sacB |
| 65 | 0.0981 | 1.2 | ATGAAATTGAAGTCTAA ACTATTACTCTCTTGTCT GGCTCTAAGCACTGTGT TCGTGGCAACAACTATT GCC (72) | MKLKSKLLLSC LALSTVFVATT IA (42) | phrF |
| 66 | 0.0967 | 1.2 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |
| 67 | 0.0939 | 1.1 | ATGTTGACGAAGCGCTT GCTTACTATATACATTA TGTTATTAGGGTTGATT GCATGGTTTCCAGGTGC GGCACAAGCT (73) | MLTKRLLTIYI MLLGLIAWFPG AAQA (43) | ylcvV |
| 68 | 0.0881 | 1.1 | GTGAGAAGCAAAAAATT GTGGATCAGCTTGTTGT TTGCGTTAACGTTAATC TTTACGATGGCGTTCAG CAACATGTCTGCGCAGG CT (46) | VRSKKLWISLL FALTLIFTMAFS NMSAQA (16) | aprE version 2 |
| 69 | 0.0867 | 1.0 | ATGAAACTTTTTAATCG GAAGGTCACTTTGGTTT CTCTTATCCTGATGGCT GTCTTTCAATTCTTCATG GCATTGATCATTAAACG GATTGTCATCAGT (74) | MKLFNRKVTL VSLILMAVFQF FMALIIKRIVIS (44) | ydbK |
| 70 | 0.0755 | 0.9 | ATGAAAAAACTTGTGCT TGCGTATCTATTTTAGC TGTGATTTTAAGTGGAG TAGCT (75) | MKKLVLCVSIL AVILSGVA (45) | phrK |

Figure 5:
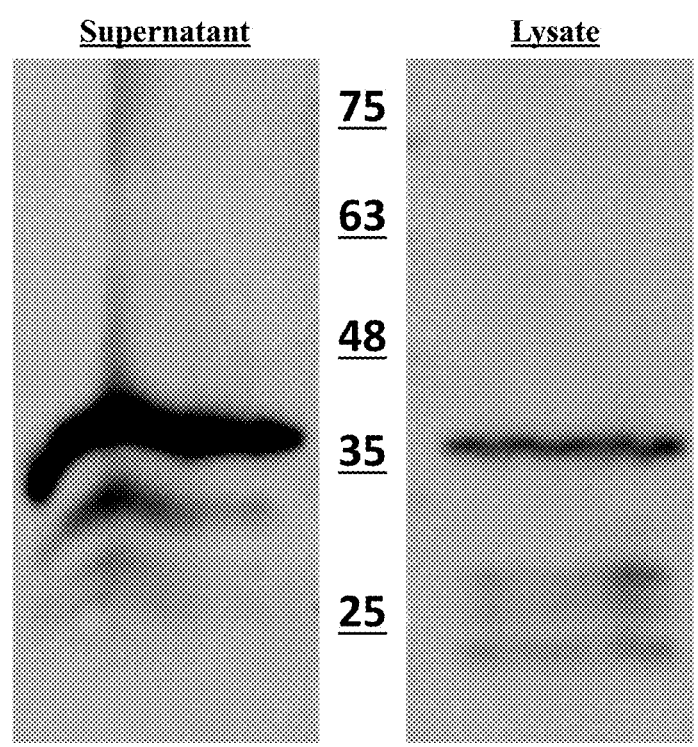
FIG. 5: is a photo of a western blot with an anti-His antibody. The supernatant from cells expressing the SP-3αHSD, as well as the cell lysate are shown. The predicted weight of 3αHSD-His is 39 kDa.

The signal peptide of colony 36 was selected for further testing as secretion was high (1.9 fold) and the signal peptide was that of a well-studied molecule (tyrA). In order to be certain that alterations to the sequence of the secreted heterologous protein did not affect its folding and correct translocation from the cell a His-tag domain was added to the C-terminus of the SP-3α-HSD protein to be secreted. This tag allowed for precise detection of the protein by western blot (predicted molecular weight-39 kDa) and clearly demonstrated secretion of 3αHSD (FIG. 5, left lane), as well as a small amount of intracellular protein (FIG. 5, right lane). The intracellular protein is likely protein still proceeded though the secretion pathway.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A polynucleotide molecule encoding a chimeric polypeptide comprising a first moiety and a second moiety, said first moiety is a dihydrotestosterone (DHT) reductase and said second moiety is a bacterial signal peptide comprising the amino acid sequence selected from the group consisting of SEQ ID NOs: 5, 16-45 or an analog thereof having at least 85% sequence identity thereto.

2. A composition comprising a first microorganism cell comprising a first polynucleotide molecule of claim 1, and any one of:
   (i) a DHT reductase cofactor;
   (ii) a second polynucleotide molecule encoding a DHT reductase cofactor producing enzyme, within said first microorganism cell; and
   (iii) a second microorganism cell, wherein said second microorganism cell comprises a second polynucleotide molecule encoding a DHT reductase cofactor producing enzyme.

3. The composition of claim 2, wherein the first microorganism cell is capable of expressing and secreting said chimeric polypeptide.

4. The composition of claim 3, wherein said DHT reductase cofactor is selected from NADPH and NADH.

5. The composition of claim 3, wherein said DHT reductase cofactor producing enzyme is Glucose-6-phosphate 1-dehydrogenase (Zwf).

6. The composition of claim 2, wherein said first microorganism cell is selected from the group consisting of: *Bacillus, Staphylococcus, Actinobacteria, Firmicutes, Proteobacteria, Bacteroidetes, Propionibacteria, Corynebacteria, Flavobacteria, lactobacillus, Escherichia coli, bifidobacteria, bacteroides*, and *Brevibacterium linens*.

7. The composition of claim 2, wherein said first microorganism cell is a *Bacillus* bacterium.

8. A kit for treating an androgen-dependent disorder, the kit comprising a first composition comprising a first microorganism cell, said first microorganism cell comprises a first polynucleotide sequence encoding a chimeric polypeptide comprising a first moiety and a second moiety, said first moiety is a dihydrotestosterone (DHT) reductase and said second moiety is a bacterial signal peptide comprising the amino acid sequence selected from the group consisting of SEQ ID NOs: 5, 16-45 or an analog thereof having at least 85% sequence identity thereto, and a second composition comprising any one of:
   (i) a DHT reductase cofactor; and
   (ii) a second microorganism cell, wherein said second microorganism cell comprises a second polynucleotide molecule encoding a DHT reductase cofactor producing enzyme.

9. The kit of claim 8, wherein said DHT reductase is 3 alpha HSD (3α-HSD) or an analog thereof.

10. A method for treating or ameliorating an androgen-dependent disorder in a subject in need thereof, the method comprising administering a first composition comprising a first microorganism cell, said first microorganism cell comprises a first polynucleotide molecule of claim 1, thereby treating or ameliorating an androgen-dependent disorder in said subject.

11. The method of claim 10, wherein said DHT reductase is 3 alpha HSD (3α-HSD) or a homolog thereof.

12. The method of claim 10, further comprising administering to the subject and a second composition, said second composition being selected from (i) a composition comprising a DHT reductase cofactor; and (ii) a composition comprising a second microorganism cell, said second microorganism cell comprises a second polynucleotide encoding a DHT reductase cofactor producing enzyme.

13. The method of claim 10, wherein said androgen-dependent disorder is androgenic alopecia.

14. The method of claim 10, wherein said administering is topically applying to the scalp of said subject.

* * * * *